US012672902B2

(12) United States Patent
Biester et al.

(10) Patent No.: US 12,672,902 B2
(45) Date of Patent: Jul. 7, 2026

(54) COMBINATION DEROTATION AND REDUCER INSTRUMENTS AND METHODS

(71) Applicant: Medos International Sárl, Le Locle (CH)

(72) Inventors: Eric Biester, Barrington, RI (US); Christopher Mickiewicz, Bridgewater, MA (US); Kevin Yeamans, Providence, RI (US); Michael Sorrenti, Middleboro, MA (US)

(73) Assignee: Medos International Sarl, Le Locle (CH)

( * ) Notice: Subject to any disclaimer, the term of this patent is extended or adjusted under 35 U.S.C. 154(b) by 0 days.

(21) Appl. No.: 18/915,551

(22) Filed: Oct. 15, 2024

(65) Prior Publication Data

US 2025/0120754 A1 Apr. 17, 2025

Related U.S. Application Data

(60) Provisional application No. 63/590,619, filed on Oct. 16, 2023.

(51) Int. Cl.
| | |
|---|---|
| *A61B 17/70* | (2006.01) |
| *A61B 17/00* | (2006.01) |
| *A61B 17/56* | (2006.01) |

(52) U.S. Cl.
CPC ...... *A61B 17/7086* (2013.01); *A61B 17/7077* (2013.01); *A61B 2017/0046* (2013.01); *A61B 2017/564* (2013.01)

(58) Field of Classification Search
CPC .............. A61B 17/7077; A61B 17/708; A61B 17/7086
See application file for complete search history.

(56) References Cited

U.S. PATENT DOCUMENTS

| | | |
|---|---|---|
| 5,443,467 A | 8/1995 | Biedermann et al. |
| 6,736,820 B2 | 5/2004 | Biedermann et al. |

(Continued)

FOREIGN PATENT DOCUMENTS

| | | |
|---|---|---|
| CN | 101052357 A | 10/2007 |
| CN | 101128158 B | 10/2010 |

(Continued)

OTHER PUBLICATIONS

[NoAuthorListed] Expedium Spine System Surgical Technique Guide, DePuy Spine Inc., 2011, 36 pages.

(Continued)

*Primary Examiner* — Julianna N Harvey

(74) *Attorney, Agent, or Firm* — Barnes & Thornburg LLP

(57) ABSTRACT

Surgical instruments and related methods are disclosed for performing rod reduction, derotation, and/or setscrew insertion during spinal surgery. One example instrument that can accommodate performing all of these functions can include an inner sleeve having a proximal threaded portion, a distal portion configured to rotate relative to the proximal threaded portion, an inner channel, and a modular drive interface disposed at a proximal end of the threaded portion. The instrument can further include an intermediate sleeve having an inner channel with a threaded proximal portion configured to receive the inner sleeve, the intermediate sleeve terminating in a pair of extensions at a distal end thereof. The instrument can further include an outer sleeve having an inner channel configured to receive the intermediate sleeve, the outer sleeve terminating in a pair of extensions at a distal end thereof.

20 Claims, 28 Drawing Sheets

(56) References Cited

U.S. PATENT DOCUMENTS

| | | | |
|---|---|---|---|
| 6,974,460 | B2 | 12/2005 | Carbone et al. |
| 7,179,261 | B2 | 2/2007 | Sicvol et al. |
| 7,618,444 | B2 | 11/2009 | Shluzas |
| 7,918,858 | B2 | 4/2011 | Stad et al. |
| 8,137,356 | B2 | 3/2012 | Hestad et al. |
| 8,206,395 | B2 | 6/2012 | McLean et al. |
| 8,246,623 | B2 | 8/2012 | Peultier et al. |
| 8,273,089 | B2 | 9/2012 | Jackson |
| 8,303,595 | B2 | 11/2012 | Jones |
| 8,308,774 | B2 | 11/2012 | Hoffman et al. |
| 8,439,924 | B1 | 5/2013 | McBride et al. |
| 8,460,308 | B2 | 6/2013 | Marino et al. |
| 8,540,718 | B2 | 9/2013 | Dauster et al. |
| 8,556,903 | B2 | 10/2013 | Miller et al. |
| 8,556,904 | B2 | 10/2013 | Rezach et al. |
| 8,845,649 | B2 | 9/2014 | Jackson |
| 8,906,062 | B2 | 12/2014 | Nichols et al. |
| 8,986,349 | B1 | 3/2015 | German et al. |
| 9,060,817 | B2 | 6/2015 | Justis |
| 9,066,761 | B2 | 6/2015 | McBride et al. |
| 9,078,709 | B2 | 7/2015 | McBride |
| 9,149,307 | B2 | 10/2015 | Sandstrom et al. |
| 9,186,188 | B2 | 11/2015 | Gleason et al. |
| 9,204,909 | B2 | 12/2015 | Rezach et al. |
| 9,220,539 | B2 | 12/2015 | McBride et al. |
| 9,220,543 | B2 | 12/2015 | Walker et al. |
| 9,241,743 | B2 | 1/2016 | Hopkins et al. |
| 9,247,969 | B2 | 2/2016 | Nunley et al. |
| 9,265,533 | B2 | 2/2016 | Nelson et al. |
| 9,468,474 | B2 | 10/2016 | Parikh et al. |
| 9,517,099 | B2 | 12/2016 | Bess et al. |
| 9,743,962 | B2 | 8/2017 | Viart et al. |
| 9,833,268 | B2 | 12/2017 | Walker |
| 9,901,378 | B2 | 2/2018 | Dauster et al. |
| 9,918,752 | B2 | 3/2018 | Hennard et al. |
| 9,943,343 | B2 | 4/2018 | Meyer et al. |
| 9,962,197 | B2 | 5/2018 | Dandaniopoulos et al. |
| 10,028,771 | B2 | 7/2018 | Artaki et al. |
| 10,039,578 | B2 | 8/2018 | Anderson et al. |
| 10,064,662 | B2 | 9/2018 | Gunn et al. |
| 10,085,778 | B2 | 10/2018 | Semingson et al. |
| 10,154,862 | B2 | 12/2018 | Miller et al. |
| 10,166,050 | B2 | 1/2019 | Heuer |
| 10,299,839 | B2 | 5/2019 | Sicvol et al. |
| 10,398,481 | B2 | 9/2019 | Goel et al. |
| 10,433,884 | B2 | 10/2019 | Barrett et al. |
| 10,524,843 | B2 | 1/2020 | Mladenov et al. |
| 10,568,669 | B2 | 2/2020 | Reitblat et al. |
| 10,610,269 | B2 | 4/2020 | Mickiewicz et al. |
| 10,675,066 | B2 | 6/2020 | George |
| 10,682,167 | B2 | 6/2020 | Sandstrom et al. |
| 10,702,315 | B2 | 7/2020 | Lindner |
| 10,709,477 | B2 | 7/2020 | Manninen et al. |
| 10,716,602 | B2 | 7/2020 | Fischer |
| 10,729,477 | B2 | 8/2020 | Cain et al. |
| 11,439,441 | B2 | 9/2022 | Mickiewicz et al. |
| 12,053,213 | B2 | 8/2024 | Mickiewicz et al. |
| 12,053,214 | B2 | 8/2024 | Biester et al. |
| 2006/0036255 | A1 | 2/2006 | Pond, Jr. et al. |
| 2006/0074418 | A1 | 4/2006 | Jackson |
| 2006/0074445 | A1 | 4/2006 | Gerber et al. |
| 2007/0093817 | A1 | 4/2007 | Barrus et al. |
| 2007/0191841 | A1 | 8/2007 | Justis et al. |
| 2007/0213714 | A1 | 9/2007 | Justis |
| 2008/0015601 | A1 | 1/2008 | Castro et al. |
| 2008/0077138 | A1 | 3/2008 | Cohen et al. |
| 2008/0228233 | A1 | 9/2008 | Hoffman et al. |
| 2009/0228053 | A1* | 9/2009 | Kolb .................. A61B 17/708 606/151 |
| 2009/0228055 | A1 | 9/2009 | Jackson |
| 2010/0114174 | A1 | 5/2010 | Jones et al. |
| 2010/0121385 | A1 | 5/2010 | Blain et al. |
| 2011/0077690 | A1 | 3/2011 | Shin et al. |
| 2011/0263945 | A1 | 10/2011 | Peterson et al. |
| 2011/0288599 | A1 | 11/2011 | Michielli et al. |
| 2012/0191144 | A1 | 7/2012 | Peultier et al. |
| 2012/0283786 | A1* | 11/2012 | Rezach .............. A61B 17/7085 606/305 |
| 2013/0018419 | A1 | 1/2013 | Rezach et al. |
| 2013/0053901 | A1 | 2/2013 | Cormier et al. |
| 2013/0096618 | A1 | 4/2013 | Chandanson et al. |
| 2013/0103039 | A1 | 4/2013 | Hopkins et al. |
| 2013/0103094 | A1 | 4/2013 | Beale et al. |
| 2013/0238030 | A1 | 9/2013 | Steib |
| 2013/0317558 | A1 | 11/2013 | Varieur et al. |
| 2014/0052197 | A1 | 2/2014 | McBride et al. |
| 2014/0074106 | A1 | 3/2014 | Shin |
| 2014/0142585 | A1 | 5/2014 | Rutledge |
| 2014/0148865 | A1 | 5/2014 | Hennard et al. |
| 2014/0180298 | A1 | 6/2014 | Stevenson et al. |
| 2014/0276894 | A1 | 9/2014 | Ramsay et al. |
| 2014/0276896 | A1 | 9/2014 | Harper |
| 2014/0277167 | A1 | 9/2014 | Hutton et al. |
| 2014/0277170 | A1 | 9/2014 | Barrett et al. |
| 2014/0277206 | A1 | 9/2014 | Reitblat et al. |
| 2014/0311264 | A1 | 10/2014 | Black et al. |
| 2014/0316475 | A1 | 10/2014 | Parikh et al. |
| 2015/0039035 | A1 | 2/2015 | Krüger |
| 2015/0066042 | A1 | 3/2015 | Cummins et al. |
| 2015/0066089 | A1 | 3/2015 | Nelson et al. |
| 2015/0112397 | A1 | 4/2015 | Petit |
| 2015/0142067 | A1 | 5/2015 | Bess et al. |
| 2015/0148849 | A1 | 5/2015 | Abidin |
| 2015/0173807 | A1 | 6/2015 | Artaki et al. |
| 2015/0351810 | A1 | 12/2015 | Lindner et al. |
| 2016/0022317 | A1 | 1/2016 | Kraus |
| 2016/0030093 | A1 | 2/2016 | Walker |
| 2016/0089188 | A1 | 3/2016 | McBride, Jr. et al. |
| 2016/0235450 | A1 | 8/2016 | Walker et al. |
| 2016/0367296 | A1 | 12/2016 | Walker |
| 2017/0100116 | A1 | 4/2017 | Erramilli et al. |
| 2017/0143385 | A1 | 5/2017 | Biyani et al. |
| 2017/0164980 | A1 | 6/2017 | Le Roux et al. |
| 2018/0055545 | A1 | 3/2018 | Biedermann et al. |
| 2018/0116703 | A1 | 5/2018 | Schäfer et al. |
| 2018/0185072 | A1* | 7/2018 | Rubin ................ A61B 17/7032 |
| 2019/0069934 | A1 | 3/2019 | Mickiewicz et al. |
| 2019/0117280 | A1 | 4/2019 | Avidano et al. |
| 2019/0183542 | A1 | 6/2019 | Lish et al. |
| 2019/0231400 | A1 | 8/2019 | Jackson et al. |
| 2019/0274740 | A1 | 9/2019 | Stoll et al. |
| 2019/0380748 | A1 | 12/2019 | Doose et al. |
| 2019/0380750 | A1 | 12/2019 | Morris |
| 2020/0093521 | A1 | 3/2020 | Klausman et al. |
| 2020/0205864 | A1 | 7/2020 | Mickiewicz et al. |
| 2020/0367939 | A1 | 11/2020 | Loftis et al. |
| 2022/0280200 | A1 | 9/2022 | Mickiewicz et al. |
| 2022/0280207 | A1 | 9/2022 | Biester et al. |
| 2023/0085069 | A1 | 3/2023 | Mickiewicz et al. |
| 2024/0382238 | A1 | 11/2024 | Mickiewicz et al. |
| 2024/0382240 | A1 | 11/2024 | Biester et al. |

FOREIGN PATENT DOCUMENTS

| | | |
|---|---|---|
| CN | 1913836 B | 11/2010 |
| CN | 103648420 A | 3/2014 |
| EP | 0249723 B1 | 7/1992 |
| JP | 2008514365 A | 5/2008 |
| JP | 2014176705 A | 9/2014 |
| WO | 2006039279 A2 | 4/2006 |
| WO | 2009158707 A1 | 12/2009 |
| WO | 2011133160 A1 | 10/2011 |
| WO | 2015140440 A1 | 9/2015 |
| WO | 2015145343 A1 | 10/2015 |

OTHER PUBLICATIONS

A Solutions for Simple and Complex Spine Pathology MATRIX Spine System Degenerative Surgical Technique (2017) DePuySynthes.
Chinese Office Action for Application No. 201880057651.0, dated Feb. 21, 2023 (17 pages).
European Examination Report for Application No. 18853556.1 dated Jun. 12, 2024 (6 pages).

(56) References Cited

OTHER PUBLICATIONS

International Search Report and Written Opinion for Application No. PCT/US18/47130, mailed Nov. 9, 2018 (11 pages).
International Preliminary Report and Written Opinion for Application No. PCT/EP2024/079010 date of mailing Jan. 29, 2025 (15 pages).
Extended European Search Report for Application No. 18853556.1, issued May 3, 2021 (7 pages).
Japanese Search Report for Application No. 2020-534162, issued Jun. 6, 2022 (27 pages).

* cited by examiner

COMBINATION DEROTATION AND REDUCER INSTRUMENTS AND METHODS

CROSS-REFERENCE TO RELATED APPLICATIONS

This application claims the benefit of U.S. Provisional Application No. 63/590,619, filed on Oct. 16, 2023. The entire contents of this application are incorporated by reference herein.

FIELD

This disclosure relates generally to surgical instruments and related methods of use and, more particularly, to combination instruments for performing vertebral derotation and rod reduction during spinal surgery, along with facilitating other functions like setscrew insertion, etc.

BACKGROUND

Fixation systems can be used in orthopedic surgery or neurosurgery to maintain a desired spatial relationship between multiple bones or bone fragments. For example, various conditions of the spine, such as fractures, deformities, and degenerative disorders, can be treated by attaching a spinal fixation system to one or more vertebrae. A typical spinal fixation system can include bone anchors implanted in the vertebrae and longitudinal rods that are secured to the bone anchors by setscrews or other closure mechanisms. A common operation performed during a spinal surgery is derotation, which involves the manipulation of the position of one or more vertebrae via instrumentation coupled thereto in order to correct a deformity, improve curvature of the spine, etc. Aside from or in addition to derotation, implanting a fixation system can involve multiple steps, e.g., bone anchor implantation, rod insertion, rod reduction into one or more bone anchors, and setscrew insertion to lock a rod relative to one or more anchors, among others.

Conventional instruments and systems have traditionally relied upon multiple separate instruments to perform these steps. For example, current solutions exist in which rod reduction is performed with a first instrument and spinal derotation is achieved via separate instrumentation. Accordingly, a large number of instruments must be prepared and made available during the surgery, the surgeon repeatedly switches between several different instruments, and frequent insertion, removal, and re-insertion of instruments to and from the surgical site can be required. All of this can lead to surgeon fatigue, prolonged operating time, increased cost, etc.

Accordingly, there is a need for improved surgical instrumentation that streamlines implantation of a fixation system and use thereof to correct spinal abnormalities by reducing a number of instruments involved.

SUMMARY

Surgical instruments and related methods are disclosed herein, e.g., for performing rod reduction, derotation, and/or setscrew insertion during spinal surgery. One example instrument that can accommodate performing all of these functions can include an inner sleeve with a proximal threaded portion, a distal portion configured to rotate relative to the proximal threaded portion, and an inner channel. The instrument can also include an intermediate sleeve having an inner channel with a threaded proximal portion configured to receive the inner sleeve. The intermediate sleeve can terminate in a pair of extensions at a distal end thereof. The instrument can further include an outer sleeve having an inner channel configured to receive the intermediate sleeve. The outer sleeve can terminate in a pair of extensions at a distal end thereof. The pair of extensions of the intermediate sleeve can each include a movable arm configured to extend into the inner channel of the intermediate sleeve and facilitate coupling to an implant disposed between the pair of extensions of the intermediate sleeve. Further, the pair of extensions of the outer sleeve can be configured such that, when the outer sleeve is advanced distally relative to the intermediate sleeve, the pair of extensions of the outer sleeve cover the pair of extensions of the intermediate sleeve and prevent the movable arms of the intermediate sleeve from moving radially outward and, when the outer sleeve is retracted proximally relative to the intermediate sleeve, the pair of extensions of the outer sleeve expose the pair of extensions of the intermediate sleeve and allow the movable arms of the intermediate sleeve to move radially outward. A setscrew or closure mechanism, and a driver instrument for applying the setscrew or closure mechanism to the bone anchor assembly, can be inserted through one or more of the working channels.

In another example, a surgical instrument can include an inner sleeve having a proximal threaded portion, a distal portion configured to rotate relative to the proximal threaded portion, an inner channel, and a modular drive interface disposed at a proximal end of the threaded portion. The instrument can further include an intermediate sleeve having an inner channel with a threaded proximal portion configured to receive the inner sleeve, the intermediate sleeve terminating in a pair of extensions at a distal end thereof. The instrument can further include an outer sleeve having an inner channel configured to receive the intermediate sleeve, the outer sleeve terminating in a pair of extensions at a distal end thereof. Moreover, the pair of extensions of the intermediate sleeve can each include a movable arm configured to extend into the inner channel of the intermediate sleeve and facilitate coupling to an implant disposed between the pair of extensions of the intermediate sleeve. Still further, the pair of extensions of the outer sleeve can be configured such that, when the outer sleeve is advanced distally relative to the intermediate sleeve, the pair of extensions of the outer sleeve cover the pair of extensions of the intermediate sleeve and prevent the movable arms of the intermediate sleeve from moving radially outward and, when the outer sleeve is retracted proximally relative to the intermediate sleeve, the pair of extensions of the outer sleeve expose the pair of extensions of the intermediate sleeve and allow the movable arms of the intermediate sleeve to move radially outward.

Any of a variety of alternative or additional features can be included and are considered within the scope of the present disclosure. For example, in some embodiments, the intermediate sleeve can include a longitudinally extending channel formed in an outer surface thereof and the outer sleeve can include a movable arm configured to extend into the channel of the intermediate sleeve to guide movement of the outer sleeve relative to the intermediate sleeve. In certain embodiments, the channel of the intermediate sleeve can include detents formed at proximal and distal ends thereof configured to preferentially seat the movable arm of the outer sleeve at the proximal and distal ends of the channel. In some embodiments, the channel can include a central portion with ramped sidewalls to facilitate ejection of the movable arm of the outer sleeve from the channel of the intermediate sleeve when the portion of the movable arm of the outer sleeve is disposed within the central portion of the channel and the outer sleeve is rotated relative to the intermediate sleeve. In certain embodiments, the instrument can further include an indicator formed on a surface of the intermediate sleeve that demarcates a position of the outer sleeve relative to the intermediate sleeve wherein the movable arm of the outer sleeve is disposed within the central portion of the channel of the intermediate sleeve.

In some embodiments, the intermediate sleeve can include two opposed channels formed in the outer surface thereof and the outer sleeve includes two opposed movable arms configured to extend into the two opposed channels of the intermediate sleeve.

In certain embodiments, the instrument can further include one or more indicators formed on a surface of the intermediate sleeve that demarcate one or more of a distally advanced position of the outer sleeve relative to the intermediate sleeve and a proximally retracted position of the outer sleeve relative to the intermediate sleeve.

In some embodiments, the movable arms of the intermediate sleeve can be biased radially inward to facilitate engagement with an implant disposed between the pair of extensions of the intermediate sleeve.

In certain embodiments, the distal portion of the inner sleeve further includes a longitudinal groove formed in an outer surface thereof that is configured to receive a feature protruding from an inner surface of the intermediate sleeve to prevent rotation of the distal portion of the inner sleeve relative to the intermediate sleeve.

In some embodiments, the inner channel of the inner sleeve can be sized to receive a setscrew through a proximal end thereof and allow passage of the setscrew distally through the channel and out a distal end of the inner sleeve.

In certain embodiments, the instrument can further include a counter-torque device having a mating feature that corresponds to one or more flats formed on the intermediate sleeve.

In some embodiments, the instrument can further include an extension sleeve that defines a lumen therethrough, the extension sleeve being configured to couple to the intermediate sleeve, the extension sleeve having one or more engagement surfaces that overlap with one or more flats formed on the intermediate sleeve to facilitate coupling. In certain embodiments, the extension sleeve can further include a pair of movable arms that are configured to extend into the lumen to further couple the extension sleeve to the intermediate sleeve. In some embodiments, the extension sleeve can further include a locking ring configured to selectively constrain movement of the movable arms. In some embodiments, the movable arms can be received in a circumferential groove along the intermediate sleeve.

In certain embodiments, the threaded portion of the inner sleeve can include a first threaded portion and a second threaded portion separated by a non-threaded portion.

In some embodiments, the threaded portion of the inner sleeve can be configured to be pulled and rotated to be removed from the intermediate sleeve.

In certain embodiments, the proximal end portion of the intermediate sleeve can include a circumferential groove.

In some embodiments, the instrument can further include a modular handle configured to couple with the modular drive interface at the proximal end of the inner sleeve. In certain embodiments, the modular handle can include a channel formed therein sized to receive a setscrew through a proximal end thereof and allow passage of the setscrew distally through the channel of the modular handle into the inner channel of the inner sleeve.

In certain embodiments, the outer sleeve can include at least one flat formed at a proximal end thereof.

In some embodiments, each of the pair of extensions of the intermediate sleeve can include sidewalls extending outward from inner surfaces of the pair of extensions at lateral ends thereof. In certain embodiments, the sidewalls can include medially extending protrusions that form a notch between each protrusion and the inner surface. In some embodiments, the notch can be configured to receive a portion of an implant.

In another example, a surgical method can include coupling a surgical instrument to a bone anchor implanted in a vertebra by distally advancing a pair of extensions formed at a distal end of an intermediate sleeve of the surgical instrument over the bone anchor such that movable arms formed in the pair of extensions extend into an inner channel of the intermediate sleeve and interface with a corresponding feature of the bone anchor to retain the implant relative to the intermediate sleeve. The method can further include locking the surgical instrument to the implant by distally translating an outer sleeve disposed over the intermediate sleeve to a position where a pair of extensions of the outer sleeve cover the pair of extensions of the intermediate sleeve and prevent the movable arms of the intermediate sleeve from moving radially outward. The method can also include reducing a spinal fixation rod disposed between the pair of extensions of the intermediate sleeve toward the bone anchor by rotating a proximal threaded portion of an inner sleeve disposed within the intermediate sleeve such that a distal portion of the inner sleeve contacts the spinal fixation rod and translates distally relative to the intermediate sleeve. Further, the method can include passing a setscrew through a proximal end of an inner channel of the inner sleeve and coupling the setscrew to the bone anchor after reducing the spinal fixation rod toward the bone anchor.

In another example, a surgical method can include coupling a surgical instrument to a bone anchor implanted in a vertebra by distally advancing a pair of extensions formed at a distal end of an intermediate sleeve of the surgical instrument over the bone anchor such that movable arms formed in the pair of extensions extend into an inner channel of the intermediate sleeve and interface with a corresponding feature of the bone anchor to retain the implant relative to the intermediate sleeve. The method can further include locking the surgical instrument to the implant by distally translating an outer sleeve disposed over the intermediate sleeve to a position where a pair of extensions of the outer sleeve cover the pair of extensions of the intermediate sleeve and prevent the movable arms of the intermediate sleeve from moving radially outward. The method can also include reducing a spinal fixation rod disposed between the pair of extensions of the intermediate sleeve toward the bone anchor by rotating a proximal threaded portion of an inner sleeve disposed within the intermediate sleeve such that a distal portion of the inner sleeve contacts the spinal fixation rod and translates distally relative to the intermediate sleeve. The method can further include passing a setscrew through an opening in a modular drive interface disposed at the proximal end of the inner sleeve, into an inner channel of the inner sleeve, and coupling the setscrew to the bone anchor after reducing the spinal fixation rod toward the bone anchor.

As with the instruments described above, the methods disclosed herein can include any of a variety of additional or alternative steps that are considered within the scope of the present disclosure. For example, in some embodiments the method can further include performing a derotation maneuver on the vertebra utilizing the surgical instrument coupled to the bone anchor.

In certain embodiments, the method can further include repeating the steps of the method to couple a plurality of surgical instruments to a plurality of bone anchors disposed in a plurality of vertebrae.

In some embodiments, the method can further include unlocking the surgical instrument by proximally translating the outer sleeve relative to the intermediate sleeve to a position where the pair of extensions of the intermediate sleeve are exposed and the movable arms of the intermediate sleeve can move radially outward. In certain embodiments, the method can further include separating the surgical instrument from the bone anchor by applying a proximal force to the surgical instrument and causing the movable arms of the intermediate sleeve to move radially outward and disengage from the corresponding feature of the bone anchor. In some embodiments, the method can further include separating the outer sleeve of the surgical instrument from the intermediate sleeve by positioning the outer sleeve at a midpoint between the distal position where the instrument was locked to the bone anchor and the proximal position where the instrument was unlocked and rotating the outer sleeve relative to the intermediate sleeve. In certain embodiments, the method can further include applying torque to the outer sleeve utilizing a tool that interfaces with at least one flat formed at a proximal end of the outer sleeve.

In certain embodiments, the method can further include coupling a counter-torque device to a proximal end of the intermediate sleeve.

In some embodiments, the method can further include coupling a derotation sleeve to a proximal end of the intermediate sleeve.

In certain embodiments, the method can further include pulling and rotating the inner sleeve to remove it from the intermediate sleeve.

In some embodiments, the method can further include coupling a modular handle to a proximal end of the intermediate sleeve.

The instruments and methods disclosed herein can be useful in connection with addressing a number of conditions, such as in surgical procedures that involve immobilization and stabilization of spinal segments as an adjunct to fusion in the treatment of acute and chronic instabilities or deformities resulting from degenerative disc disease, spondylolisthesis, trauma, spinal stenosis, curvatures, tumor, pseudoarthrosis, and failed previous fusion. By way of example, the instruments and devices disclosed herein can be used in the same procedures as those described in U.S. Pat. No. 10,610,269, entitled "Modular surgical instruments and related methods," and U.S. Pat. Pub. No. 2022/0280207, entitled "Sequential Reducer," the disclosures of which are hereby incorporated by reference in their entireties.

Further details are provided below. Any of the features or variations described herein can be applied to any particular aspect or embodiment of the present disclosure in a number of different combinations. The absence of explicit recitation of any particular combination is due solely to avoiding unnecessary length or repetition.

DETAILED DESCRIPTION

Figure 1A:
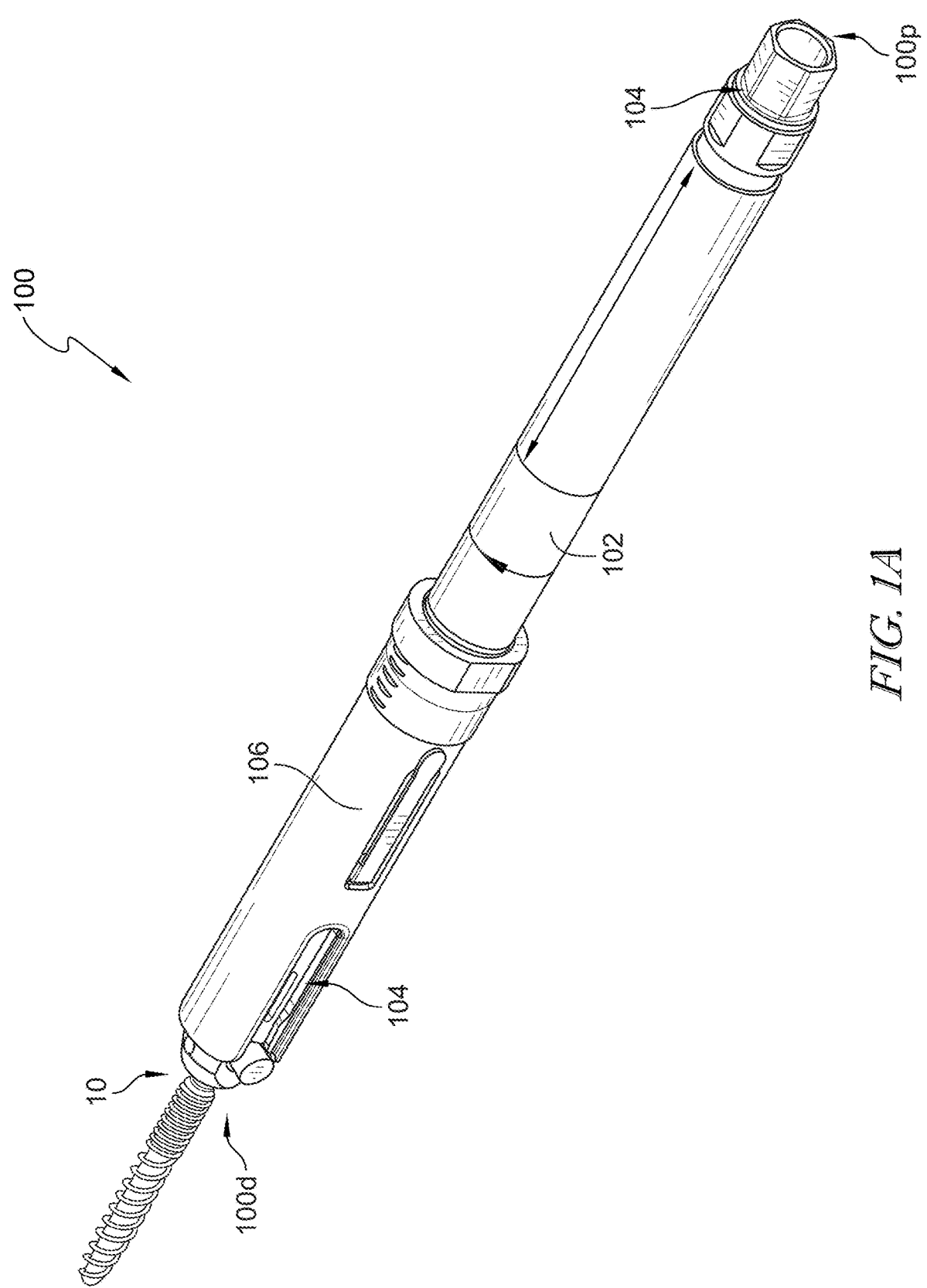
FIG. 1A is a perspective view of one embodiment of a combination derotation and reducer instrument, bone anchor, and spinal fixation element.

Certain example embodiments will now be described to provide an overall understanding of the principles of the structure, function, manufacture, and use of the devices, systems, and methods disclosed herein. One or more examples of these embodiments are illustrated in the accompanying drawings. The devices, systems, and methods specifically described herein and illustrated in the accompanying drawings are non-limiting embodiments. The features illustrated or described in connection with one embodiment may be combined with the features of other embodiments. Such modifications and variations are intended to be included within the scope of the present disclosure.

FIGS. 1A-1E illustrate perspective, exploded, and longitudinal cross-sectional views, respectively, of one embodiment of a combination derotation and reducer instrument 100. The instrument 100 can provide a platform for various surgical steps, such as rod reduction, derotation, and/or setscrew insertion, all in a single instrument. The instrument 100 can include an intermediate sleeve 102 (also referred to as a derotation sleeve or tube), an inner sleeve 104 (also referred to as a reducer sleeve or tube), and an outer sleeve or tube 106 (also referred to as a locking sleeve or tube). The intermediate sleeve 102 can define an inner or working channel 108 configured to receive at least a portion of another tool or instrument, e.g., the inner sleeve 104, therein. The channel 108 can provide access to the surgical site to allow passage of instruments or implants therethrough. The channel 108 can extend from a proximal end 100p of the instrument 100 to a distal end 100d of the instrument. The outer sleeve 106 can define an inner or working channel 110 configured to receive at least a portion of the intermediate sleeve 102 therein. The outer sleeve 106 can translate relative to the intermediate sleeve 102 to facilitate locking of the instrument 100 to a spinal fixation construct, including a spinal fixation element, such as a rod 16, and a bone anchor 10, as discussed in greater detail below.

In use, the instrument 100 can be positioned such that the intermediate sleeve 102 can engage a bone anchor 10 disposed between opposed distal extensions thereof to dock the reducer instrument 100 to the bone anchor 10. The intermediate sleeve 102 can include a pair of movable arms or fingers 116a, 116b formed in the opposed distal extensions that can extend into the lumen 108 to engage the bone anchor 10. The arms 116a, 116b can be integrally formed, e.g., welded or otherwise unitarily formed with, the intermediate sleeve 102 in a manner that allows some movement of the arms relative to the intermediate sleeve. For example, the arms 116a, 116b can be formed by cutting an elongate groove into a sidewall of the intermediate sleeve 102 that leaves an elongate portion of the arm coupled to the remainder of the intermediate sleeve via a living hinge. Alternatively, the arm can be a separate component that can be welded, adhered, fastened, or otherwise coupled to the intermediate sleeve 102 in a manner that allows some relative motion therebetween. In some embodiments, the arms can have a bias, e.g., a radially inward bias, such that they tend to extend into the inner channel 108 of the intermediate sleeve 102.

One example bone anchor 10 can include a shank 14 and a receiver head 12 into which a rod 16 can be reduced. Retention of the receiver head 12 can occur by engaging one or more notches 18 formed in the receiver head 12 with the arms 116a, 116b of the intermediate sleeve 102. As shown in FIG. 1D, the arms 116a, 116b can include extensions or hooks 115 on inner surfaces thereof that can extend into the notches 18 to facilitate coupling of the instrument 100 to the bone anchor 10.

FIGS. 2A-2D illustrate the intermediate sleeve 102 in greater detail. As shown, the intermediate sleeve 102 can include a generally tubular central portion that terminates in first and second extensions or arms 112a, 112b. The extensions 112a, 112b can have one or more recesses formed therein to receive the arms 116a, 116b or, as noted above, the arms 116a, 116b can be integrally formed with the extensions 112a, 112b, such as by cutting through the extensions 112a, 112b around a distal portion of the arms 116a, 116b while leaving a proximal portion intact as a living hinge. The intermediate sleeve 102 can be defined by a sidewall 114 circumscribing the channel 108. An interior surface of the channel 108 can be threaded or can include other mating features for cooperating with an instrument, such as the inner sleeve 104 inserted therethrough, to facilitate advancing the instrument longitudinally relative to the intermediate sleeve 102. The threading of the inner surface of the intermediate sleeve 102 can extend only along a proximal portion of the intermediate sleeve in some embodiments, e.g., as shown in the cross-sectional views of FIGS. 1D and 1E.

Figure 2A:
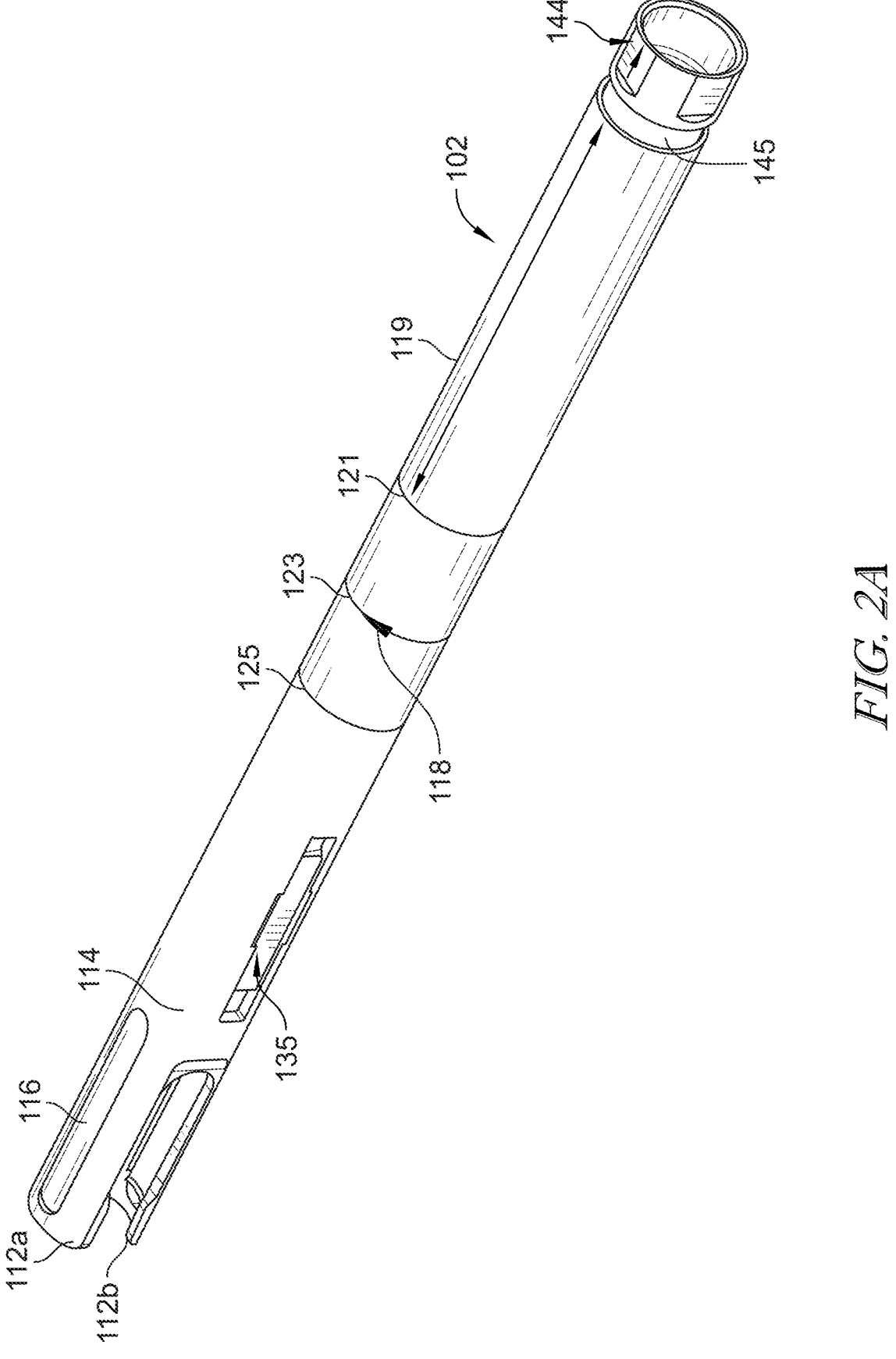
FIG. 2A is a perspective view of the intermediate sleeve of the instrument of FIG. 1A.

The intermediate sleeve 102 can include indicators 118 that show whether the instrument is in an unlocked position, locked position, and/or a removal position. For example, as shown in FIG. 2A, the intermediate sleeve 102 can include labels, text, and/or images thereon to indicate the position of the instrument 100. The intermediate sleeve 102 can include a series of lines that demarcate the relative position of the outer sleeve 106 along the intermediate sleeve 102. As shown, the indicators 118 can also mark a proximal frame clamp area 119 that extends proximally from the line 121 that marks a proximally withdrawn, unlocked position of the outer sleeve 106. The intermediate sleeve 102 can include an intermediate line 123 that reads "removal" as the indicator 119, and a distal line 125 that marks a distally advanced, locked position of the outer sleeve 106. In use, the outer sleeve 106 can translate relative to the intermediate sleeve 102 to move the instrument between an unlocked position, i.e., when the outer sleeve is proximally withdrawn relative to the intermediate sleeve 102 such that a proximal end of the outer sleeve aligns with the line 121, and a locked position, i.e., when the outer sleeve is distally advanced relative to the intermediate sleeve such that a proximal end of the outer sleeve aligns with the line 125.

The inner sleeve 104 can translate relative to the intermediate sleeve 102. The inner sleeve 104 can include a generally cylindrical shaft having a proximal end 104*p* and a distal end 104*d* with an inner or working channel or lumen 133 passing therethrough. The inner channel 110 can allow the inner sleeve 104 to be inserted over a guidewire or to allow instruments, implants, or other objects to be inserted through the inner sleeve. For example, the inner sleeve 104 can allow a setscrew or other closure mechanism, and an instrument for applying the setscrew or closure mechanism to a bone anchor, to be passed through the inner channel 133 to apply the setscrew or closure mechanism to the receiver member 12 of the bone anchor 10. The inner sleeve 104 can have an outer diameter that is smaller than an inner diameter of the channel 108 of the intermediate sleeve 102 such that the inner sleeve 104 can be inserted through the inner channel 108 of the intermediate sleeve 102. In operation, at least a portion of the inner sleeve 104 can rotate relative to the intermediate sleeve 102 about the axis A1 to advance the inner sleeve 104 distally relative to the intermediate sleeve 102 and a bone anchor 10 secured thereto, thereby urging the rod 16 towards the receiver member 12 of the bone anchor 10.

The inner sleeve 104 can include a proximal threaded portion 120 and a distal translating portion 122. The relationship between the two portions is shown in greater detail in FIGS. 1A-1E. As shown, the proximal threaded portion 120 and the distal translating portion 122 can be coupled via a series of radially oriented pins or projections 117 that can protrude from an inner surface of the threaded portion 120 and be received within a circumferential groove 127 formed in an outer surface of the distal translating portion 122. As shown, a washer 124, e.g., a thrust washer, made of a polymer or gall-resistant metallic material can separate the two portions and serve as a bearing surface between the distal translating portion 122 and the proximal threaded portion 120.

Figures 2B, 2C:
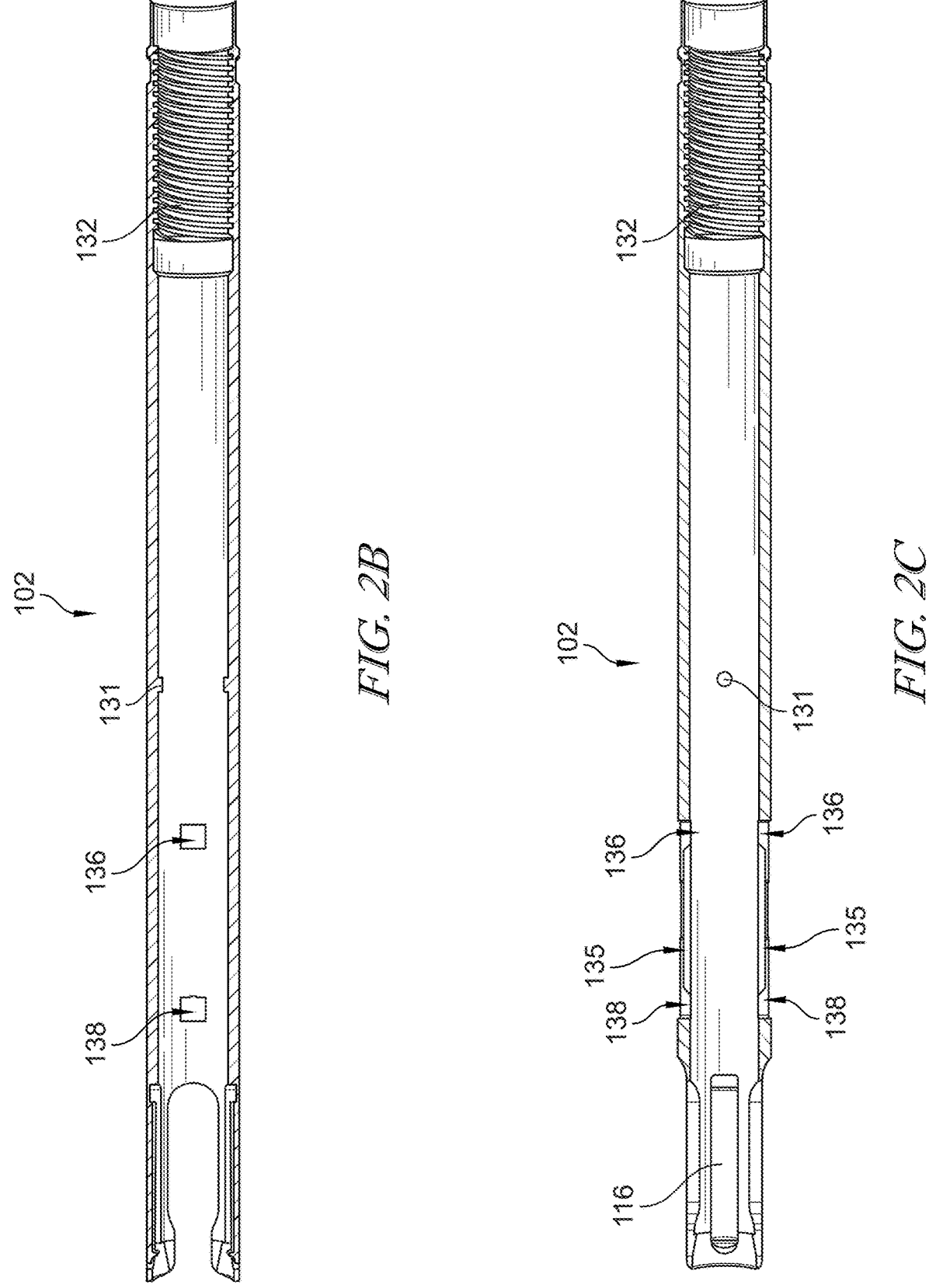
FIG. 2B is a longitudinal cross-sectional view of the intermediate sleeve of FIG. 2A.
FIG. 2C is an alternative longitudinal cross-sectional view of the intermediate sleeve of FIG. 2A.

Rotation of the distal translating portion 122 relative to the intermediate sleeve 102 can be prevented by one or more features that engage a corresponding feature of the distal translating member 122. For example, in some embodiments, the distal translating portion 122 can include one or more longitudinal grooves 129 formed therein. In some embodiments, one or more pins 131 can be placed into a through-hole formed in a sidewall of the intermediate sleeve such that it extends into the inner channel 108. As shown in FIG. 2B, the one or more pins 131 can travel within the longitudinal grooves 129 of the distal translating portion 122 and thereby prevent relative rotation between the intermediate sleeve 102 and the distal translating portion 122. In other embodiments, the pin can be a protrusion or nub integrally formed on an inner surface of the intermediate sleeve 102, such that the longitudinal grooves 129 can receive the protrusion or nub 131 to prevent rotation of the distal translating portion 122 relative to the intermediate sleeve during reduction. An integrally formed feature can be utilized in place of separate pins to minimize complexity in manufacturing and/or assembly, as well as the need for various operations, such as welding, adhering, fastening, etc.

The intermediate sleeve 102 can include a pair of grooves 135 in the sidewall 114 thereof. For example, as shown in FIGS. 1A-1E, the grooves 135 can receive a pair of movable arms 156 of the outer sleeve 106, as discussed in greater detail below. Each groove 135 can include a recessed surface or central channel 139 that terminates in a proximal detent or bore 136 and a distal detent or bore 138 formed in the sidewall 114. As shown in FIG. 2D, each of the proximal bore 136 and the distal bore 138 can be in communication with the lumen 108 while the remainder of the groove 135, e.g., the recessed surface, can terminate prior to entering the lumen 108. Each of the groove 135, the proximal bore 136, and the distal bore 138 can be configured to receive a portion of a movable arm 156 during various movements of the outer sleeve 106 relative to the intermediate sleeve 102 to selectively lock and unlock the instrument 100 to an implant 10. Each groove 135 can include a pair of ramped sidewalls or chamfered edges 141 that extend laterally from the recessed surface 139 along a central portion of the groove to allow rotation of the outer sleeve 106 relative to the intermediate sleeve 102 when a distal end of the movable arm 156 is disposed in the central portion of the groove. Rotation of the outer sleeve 106 relative to the intermediate sleeve 102 when the outer sleeve is disposed in this intermediate position can allow for disassembly of the instrument 100, for example. A detailed description of the relative movement of the outer sleeve 106 relative to the intermediate sleeve 102 is discussed in greater detail below with respect to FIGS. 13A-13C.

Figure 3:
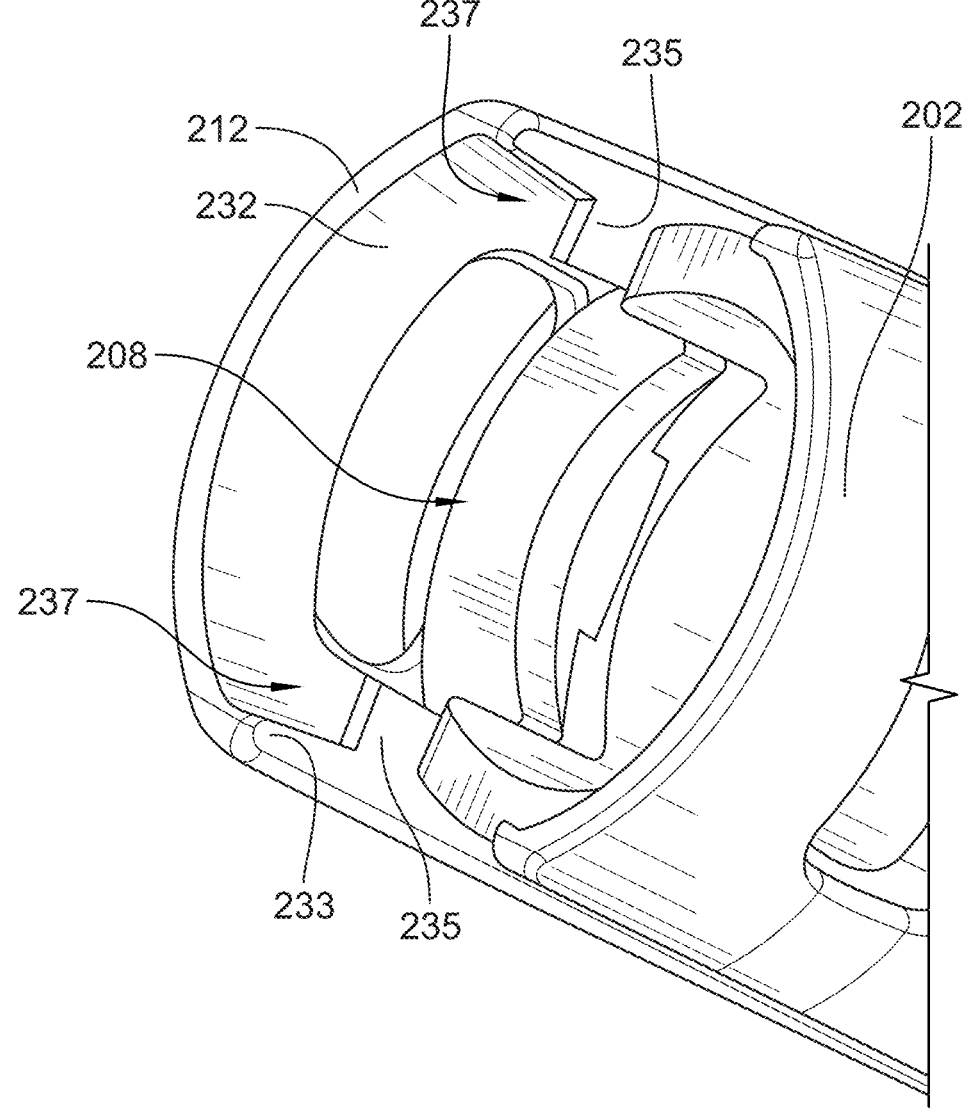
FIG. 3 is a detail view of a distal portion of one embodiment of an intermediate sleeve.

The instrument 100 can include one or more features to prevent undesirable disengagement from a bone anchor, for example, as a result of the extensions 112*a*, 112*b* splaying outward when instrument is subjected to certain loading conditions during use. FIG. 3 illustrates one embodiment of a distal end of an intermediate sleeve 202 of an instrument 200, wherein a distal portion of the extensions 212*a*, 212*b* can have an increased thickness, resulting in an increased outer diameter being carried farther toward the distal end of the arms 212*a*, 212*b*. This can increase a stiffness and strength of the arms, which can help to combat unintentional arm splaying and possible decoupling from a bone anchor during use. Alternatively or in addition, sidewalls 233 can extend from inner surfaces 232 of each extension 212 at lateral ends thereof. Further, the sidewalls 233 can include one or more medially extending protrusions 235 that can form a notch 237 between the protrusion and the inner surface 232. The notch 237 can be configured to receive a portion of a bone anchor therein. As shown in FIG. 3, the protrusions 235 can be formed on opposite sides of each extension 212. Creating the notch 237 can provide a plurality of points of contact between the extensions 212 and a bone anchor engaged therewith. Importantly, the notch also allows a portion of each extension 212 to be disposed radially inward from a portion of the bone anchor 10. This can allow the portion of the bone anchor disposed within the notch 237 to provide a bearing surface against which the extension 212 can act in resisting splaying forces that would drive the opposed extensions 212 of the intermediate sleeve 102 apart from one another.

Figure 4:
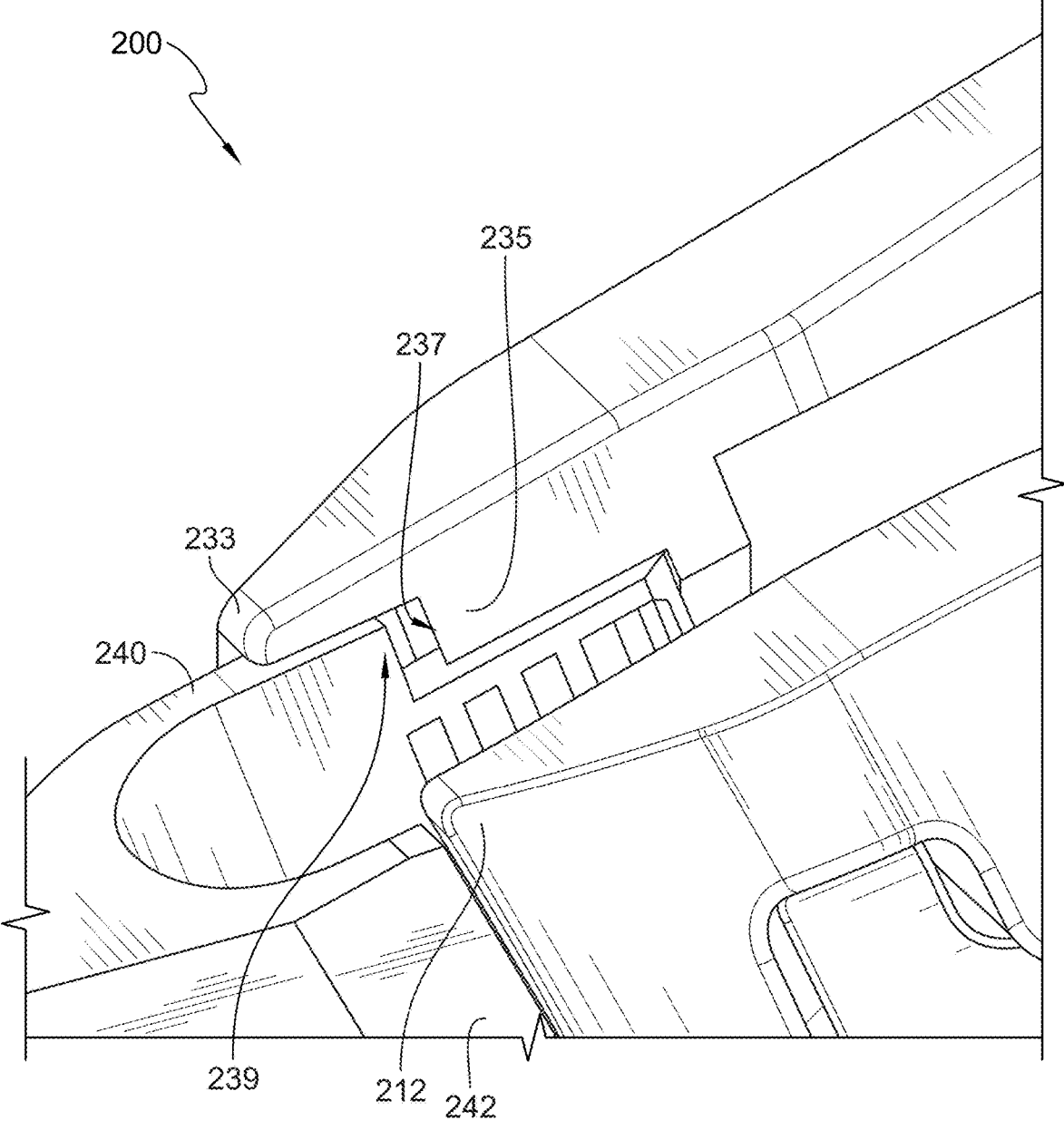
FIG. 4 is a detail view of a distal portion of one embodiment of a combination derotation and reducer instrument coupling with a bone anchor.

FIGS. 4-7 illustrate the interaction of the notches 237 with a bone anchor receiver member during coupling of the instrument 200 to the bone anchor. As shown in the detailed perspective view of FIG. 4, a proximal portion of the bone anchor receiver member 240 can be received within the notch 237 created between the inner surface 232 and the protrusion 235 of the extension 212. Because splaying forces urge the extension 212 radially outward relative to the bone anchor receiver member 240, the protrusion 235 disposed radially inward of one of the opposed arms 242 of the bone anchor receiver member 240 can effectively resist any radially-outward movement of the extension 212. The bone anchor receiver member 240 can include one or more notches 239 formed at lateral ends of its opposed arms 242 that can be configured to receive the protrusion 235 in a dovetail arrangement without reducing a width of a rod slot opening between the opposed arms 242 of the receiver member 240. When disposed as shown in FIG. 4, the instrument 200 can withstand high loads in different directions, such as those that occur during spinal rod reduction and derotation maneuvers, without decoupling from the bone anchor 10 because the protrusion 235 abuts the sidewalls of the corresponding bone anchor notch 239 to prevent splaying of the extension 212.

Figure 5:
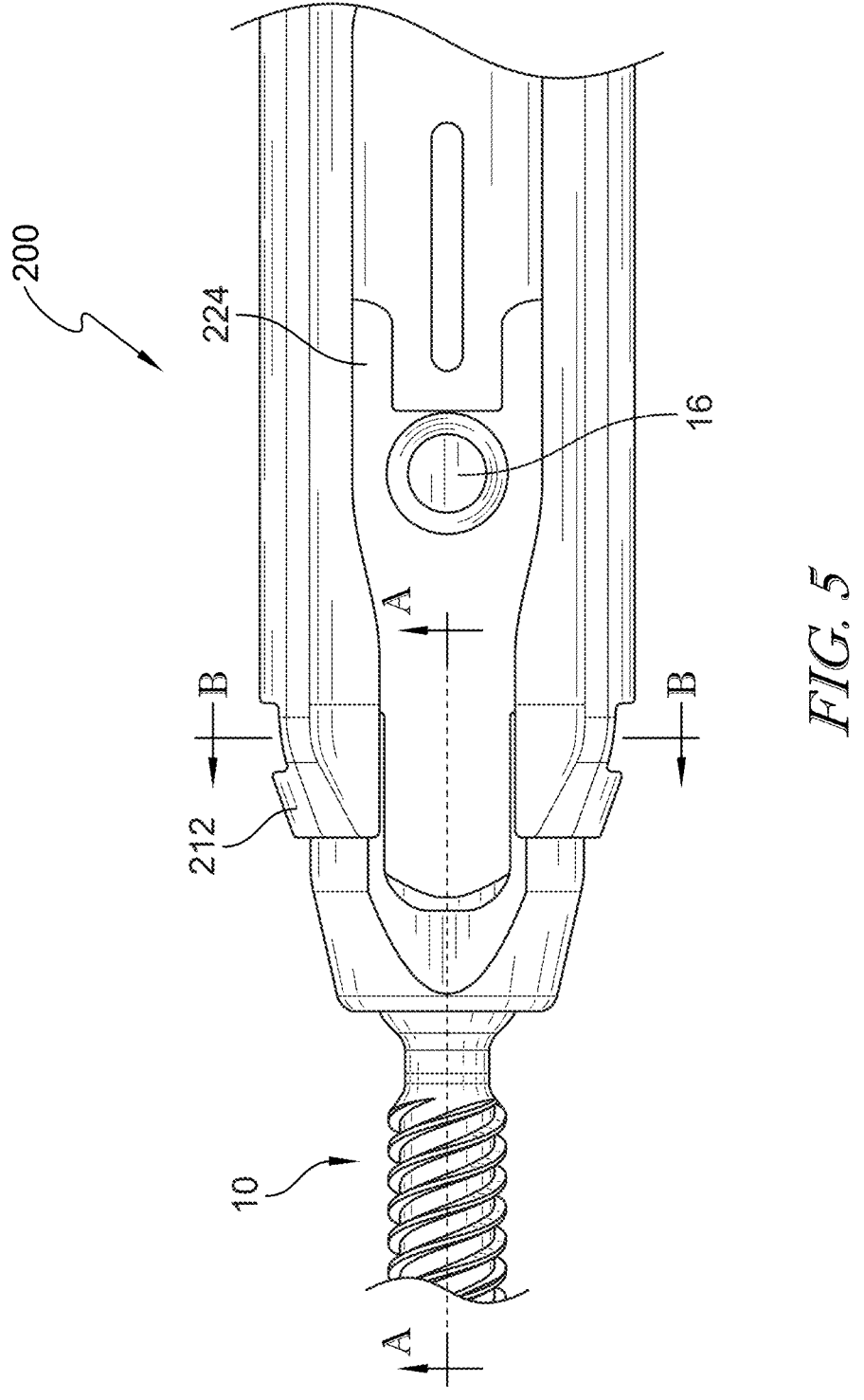
FIG. 5 is a side view of the instrument and bone anchor of FIG. 4 reducing a spinal fixation rod.

FIG. 5 illustrates a side view of the instrument 200 coupled to a bone anchor 10 and reducing a spinal fixation rod 16. As shown in this figure, the intermediate sleeve 202 includes a rod capture opening 224 between the extensions 212a, 212b that has a larger width along a proximal portion thereof and tapers to a narrower width distally. This configuration can permit greater tolerance for rotational and/or lateral misalignment of the rod and instrument that can be gradually corrected as the rod is axially reduced toward a bone anchor. In some embodiments, the transition between the larger and narrower rod capture opening widths can be gradual or smooth to prevent the rod from binding against a more abrupt transition (e.g., a step or a small-diameter curved transition).

Figure 6:
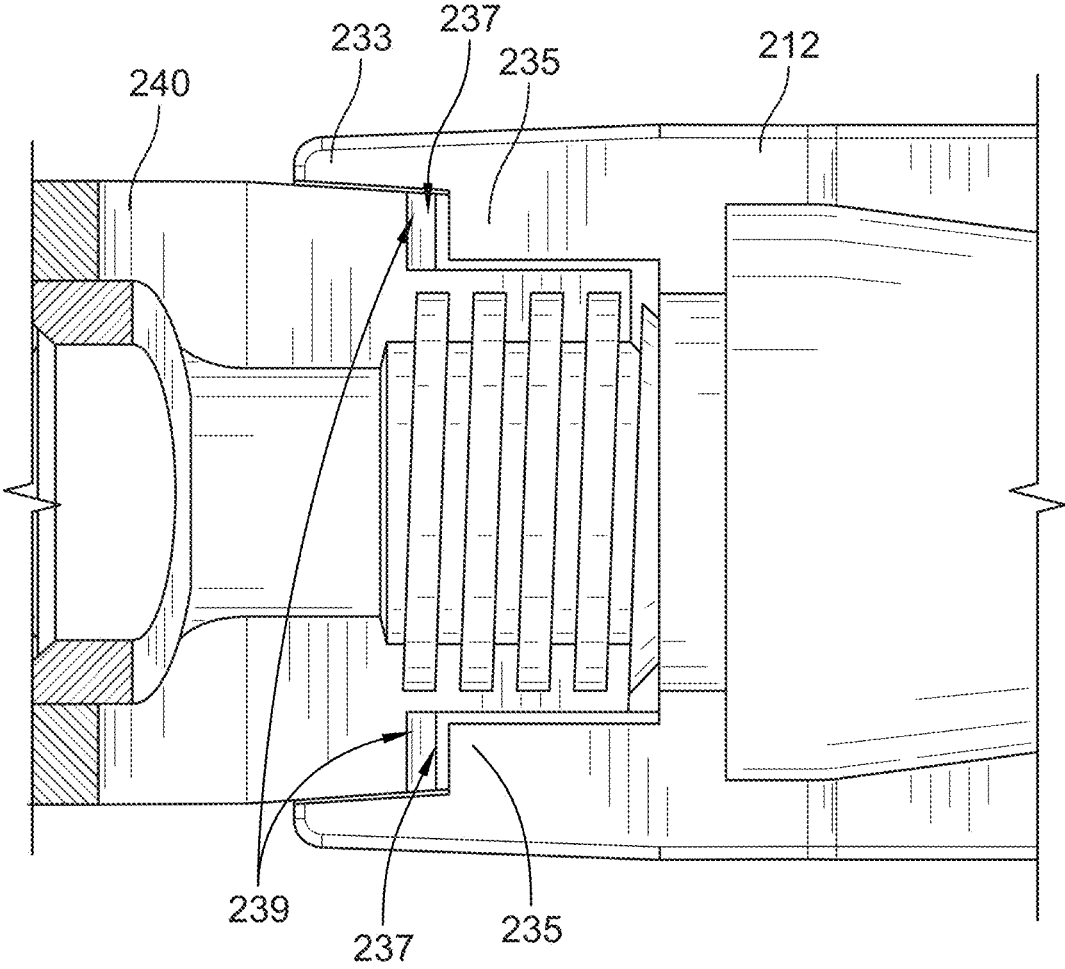
FIG. 6 is a cross-sectional view of the instrument and bone anchor of FIG. 4 taken along the line A-A in FIG. 5.

FIG. 6 illustrates a cross-sectional view of the instrument 200 and bone anchor 10 taken along the line A-A in FIG. 5. Similar to FIG. 4, the protrusions 235 can be seen disposed in the notches 239 formed in the lateral edges of the bone anchor receiver member 240, which in turn means that the arm of the receiver member 240 is disposed in the notches 237 formed between the protrusions 235 and the inner surface 232 (obstructed in this view) of the extension 212. This creates a backstop whereby the protrusions 235 can resist forces that would pull the extension 212 radially away (into the plane of the page in this view) from the receiver member 240.

Figure 7:
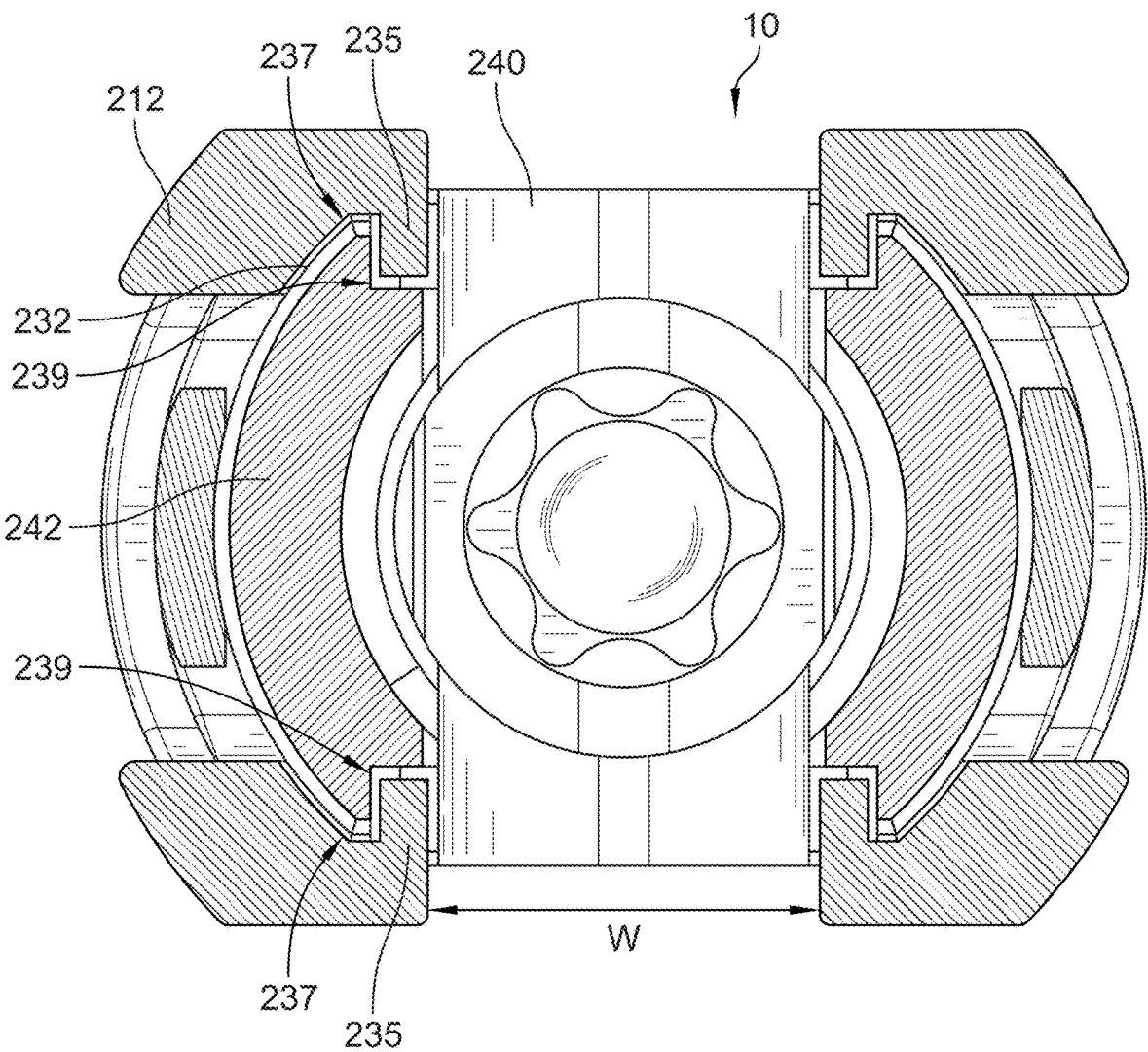
FIG. 7 is a cross-sectional view of the instrument and bone anchor of FIG. 4 taken along the line B-B in FIG. 5.

FIG. 7 illustrates a cross-sectional view of the derotation tube reducer instrument 200 and bone anchor 10 taken along the line B-B in FIG. 5. Similar to FIGS. 4 and 6, the configuration of the protrusions 235 to create notches 237 between the inner surface 232 of the extension 212 and the protrusions themselves is shown. Also shown is the portion of the bone anchor receiver member arm 242 disposed within the notches 237 such that the protrusions 235 can resist any radially outward forces (to the left and right in the plane of the page in this view) that might threaten to decouple the extensions 212 from the receiver member opposed arms 242. Finally, the figure also shows that the protrusions 235 are housed in notches 239 formed in the opposed arms 242 of the receiver member 240 such that a width W of the rod slot is not reduced. The configuration is repeated at each lateral edge of each extension 212 of the intermediate sleeve 102. Further details about the notches 237 are discussed in U.S. Pat. Pub. No. 2022/0280207, entitled "Sequential Reducer," the disclosure of which is hereby incorporated by reference in its entirety.

FIGS. 8A-8D illustrate the inner sleeve 104 disposed within the intermediate sleeve 102. The intermediate sleeve 102 can have a distal pocket or window 137 formed between the opposed extensions 112a, 112b that can accept the receiver member 12 of the bone anchor 10 and couple thereto. The distal pocket 137 can vary in size, though, in some embodiments, it can be about 9 mm wide. The size and shape of the distal end of the intermediate sleeve 102 can enable coupling to a bone anchor with some amount of lateral misalignment. Moreover, an internal surface of the extensions 112a, 112b can have a shape or profile that is complementary to an outer surface of the bone anchor in order to facilitate coupling even in the event there is some amount of misalignment, whether that be, e.g., lateral or rotational misalignment along an axis of a rod, rotational misalignment along a longitudinal axis of the instrument 100, etc. In some embodiments, for example, an inner surface of each extension 112a, 112b can include a tapered profile complementary to an outer surface of opposed arms of a polyaxial bone anchor receiver head. In some instances, the inner surface of each arm can include a conical tapering profile that is complementary to the conical tapering profile of a receiver member. Such an arrangement can allow for some pivoting misalignment between the receiver head and the instrument 100 that can be corrected as the instrument is advanced distally relative to the receiver head and the receiver head advanced into the distal pocket 137.

Further, the extensions 112a, 112b can include sidewalls extending outward from an inner surface at lateral ends of each arm. The sidewalls can similarly include a tapering profile to aid alignment with a receiver member of a bone anchor, e.g., by self-correcting for rotational misalignment about the longitudinal axis of the instrument as the instrument is advanced distally relative to the bone anchor and the anchor is received between the extensions 112a, 112b. In some embodiments, the opposed, inward-facing surfaces of each sidewall can have a planar tapering profile that can be complementary to a planar tapering profile of abutting surfaces on a bone anchor receiver member. The various tapered surfaces can accommodate misalignment when coupling the instrument 100 to the bone anchor 10 such that advancement of the intermediate sleeve 102 over the bone anchor forces the two components into proper alignment just prior to positive engagement of the arms 116a, 116b with the anchor 10 to simplify attachment of the instrument 100 to the anchor 10. As noted, the receiver member 12 can include one or more complementary tapering profiles to the tapered surfaces provided on the outer sleeve. Further details on features of the anchor 10 that can be utilized with the instruments disclosed herein can be found in U.S. Pat. Nos. 10,039,578 and 10,299,839, as well as U.S. Pat. Pub. No. 2022/0280200, entitled "Multi-Feature Polyaxial Screw." The entire contents of each of these documents are incorporated by reference herein.

A proximal end of the intermediate sleeve 102 can include one or more mating features. For example, the intermediate sleeve 102 can include one or more proximal flats 144 having a square or rectangular shape oriented around a circumference thereof. The flats 144 can be spaced around a circumference of the intermediate sleeve to couple to a corresponding mating feature of an instrument that engages the intermediate sleeve. Moreover, the intermediate sleeve can include a circumferential groove 145 that extends around the circumference of the intermediate sleeve 102 to facilitate engagement to instruments, as discussed further below. As shown, the circumferential groove 145 can be oriented distal to the flats 144, though their relative orientation can be reversed.

The distal translating portion 122 of the inner sleeve 104 can include first and second static or fixed arms 134a, 134b extending distally therefrom for performing rod reduction, as shown in FIG. 1B, FIGS. 8A-8D, and FIG. 12. The static arms 134a, 134b can be configured to advance distally without rotating relative to the intermediate sleeve 102 to advance the spinal rod into the receiver member 12. For example, the arms 134a, 134b can contact and bear against a spinal rod 16 to urge the rod distally as the inner sleeve 104 is translated distally within the instrument 100. In some embodiments, the arms 134 can include cutouts 225 to facilitate visualization of the rod during reduction. The arms 134 can be aligned with the rod slot defined between the extensions 112a, 112b of the intermediate sleeve 102 such that they can pass into the rod slot of the receiver member 12 of the bone anchor 10.

Figure 1B:
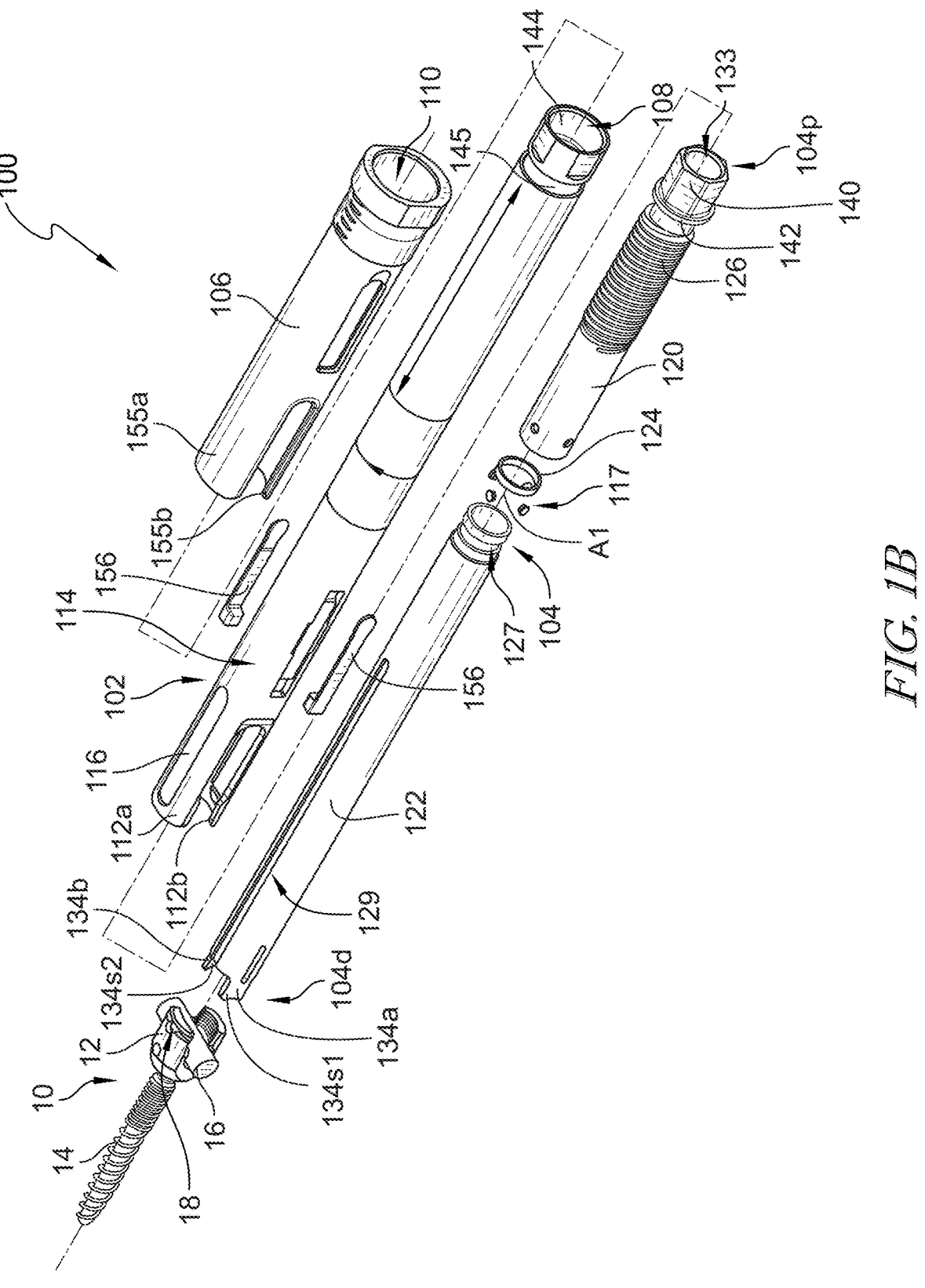
FIG. 1B is an exploded view of the instrument, bone anchor, and spinal fixation element of FIG. 1A.
Figure 1C:
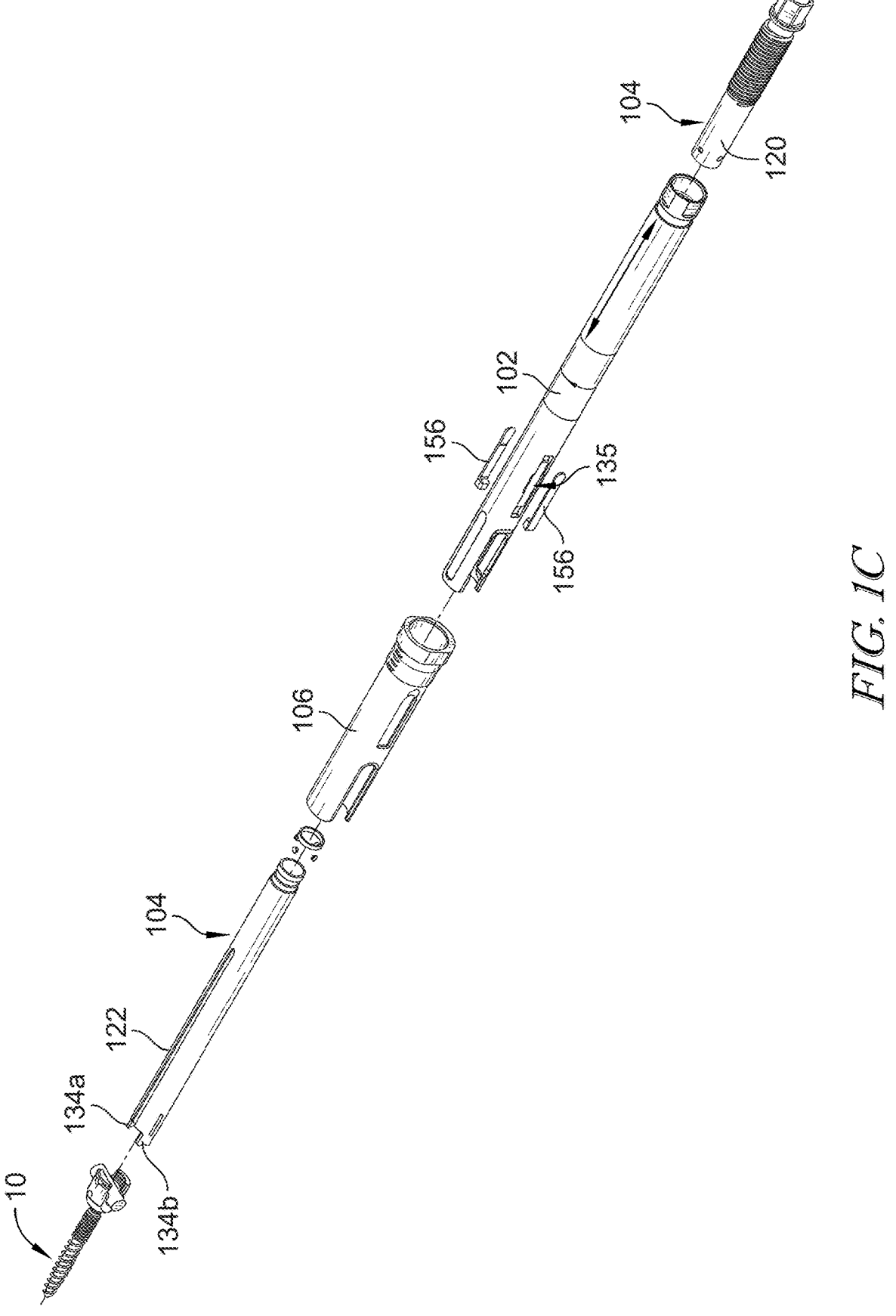
FIG. 1C is an alternative exploded view of the instrument, bone anchor, and spinal fixation element of FIG. 1A.
Figure 1D:
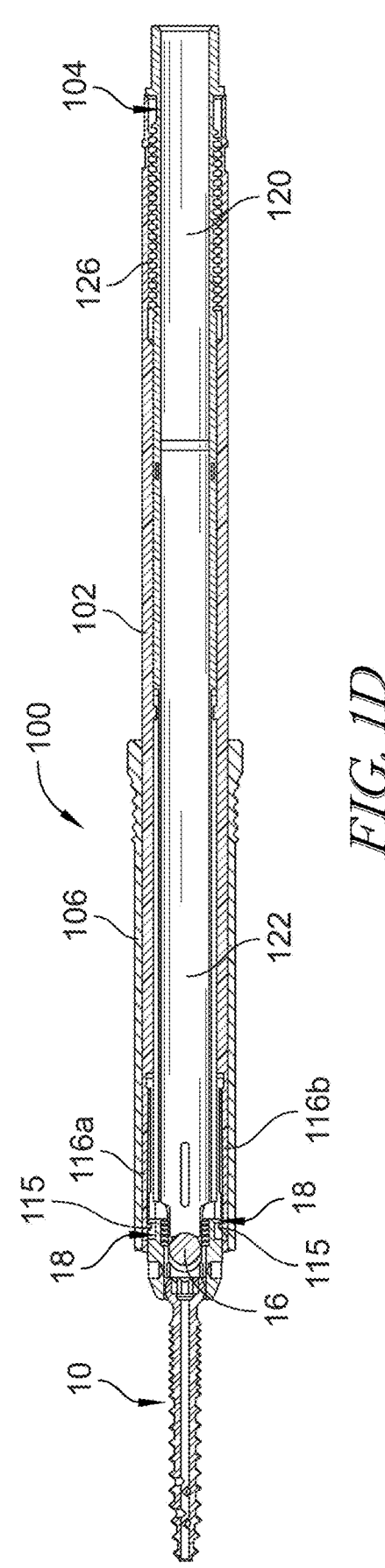
FIG. 1D is a longitudinal cross-sectional view of the instrument, bone anchor, and spinal fixation element of FIG. 1A.
Figure 1E:
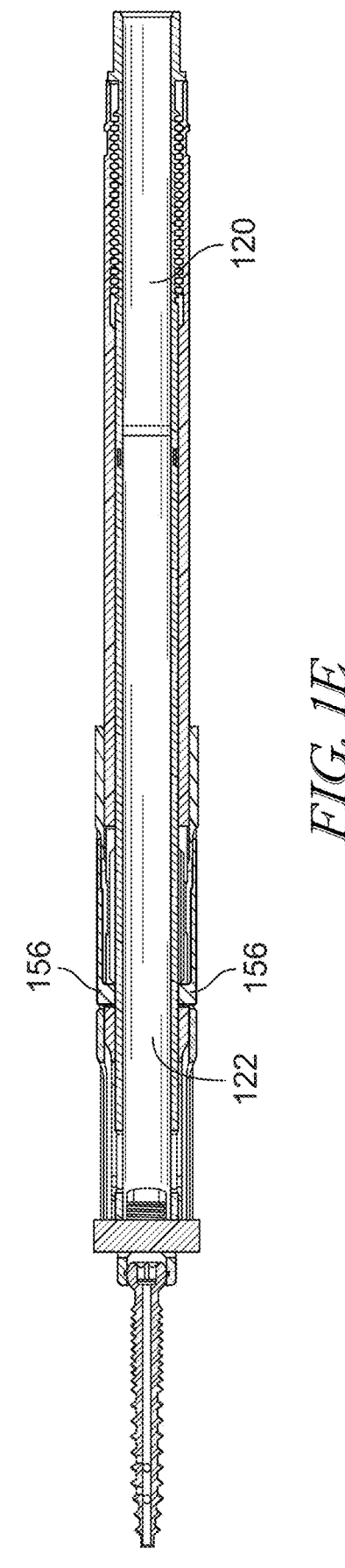
FIG. 1E is an alternative longitudinal cross-sectional view of the instrument, bone anchor, and spinal fixation element of FIG. 1A.
Figure 2D:
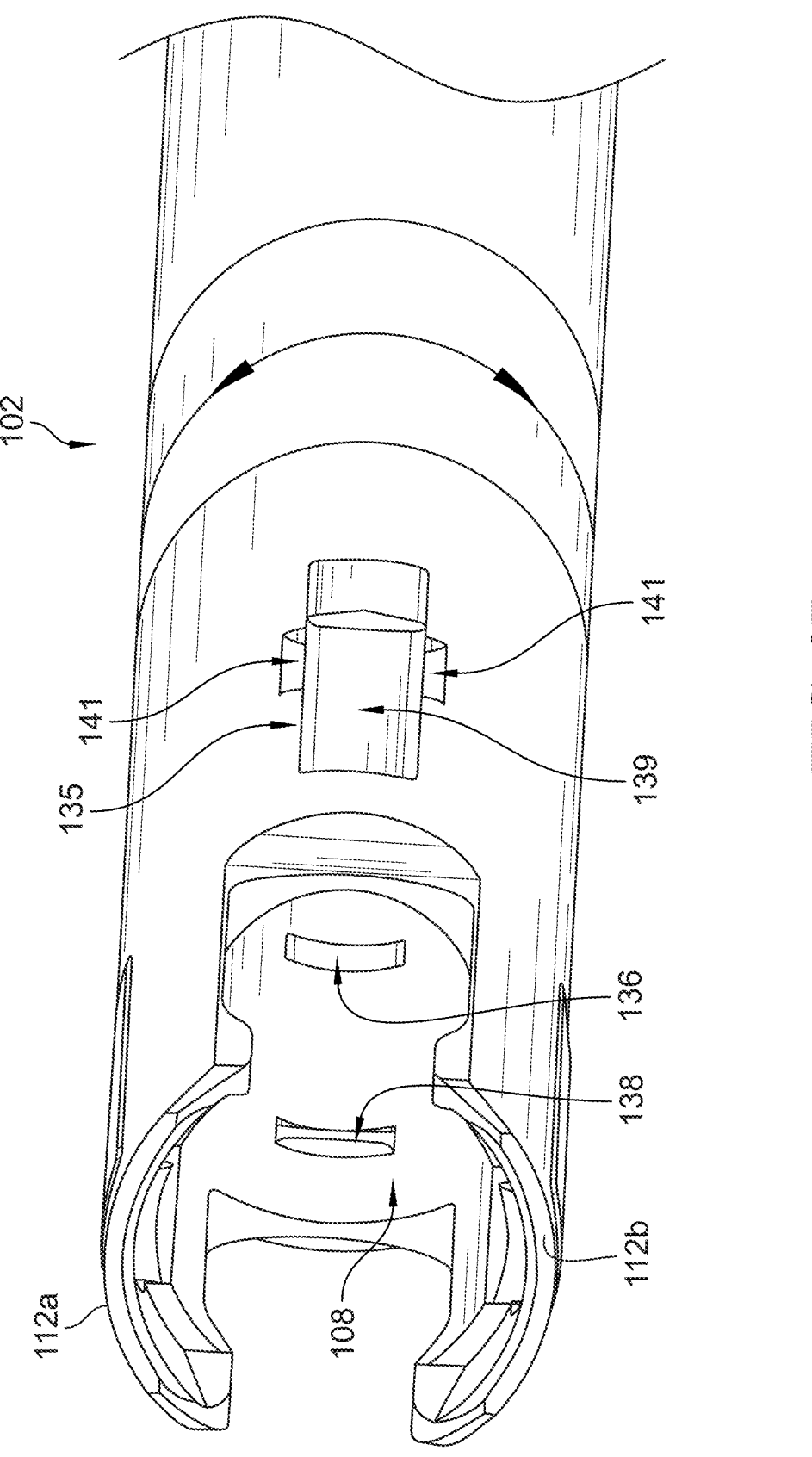
FIG. 2D is a detail view of a distal portion of the intermediate sleeve of FIG. 2A.
Figures 9, 10:
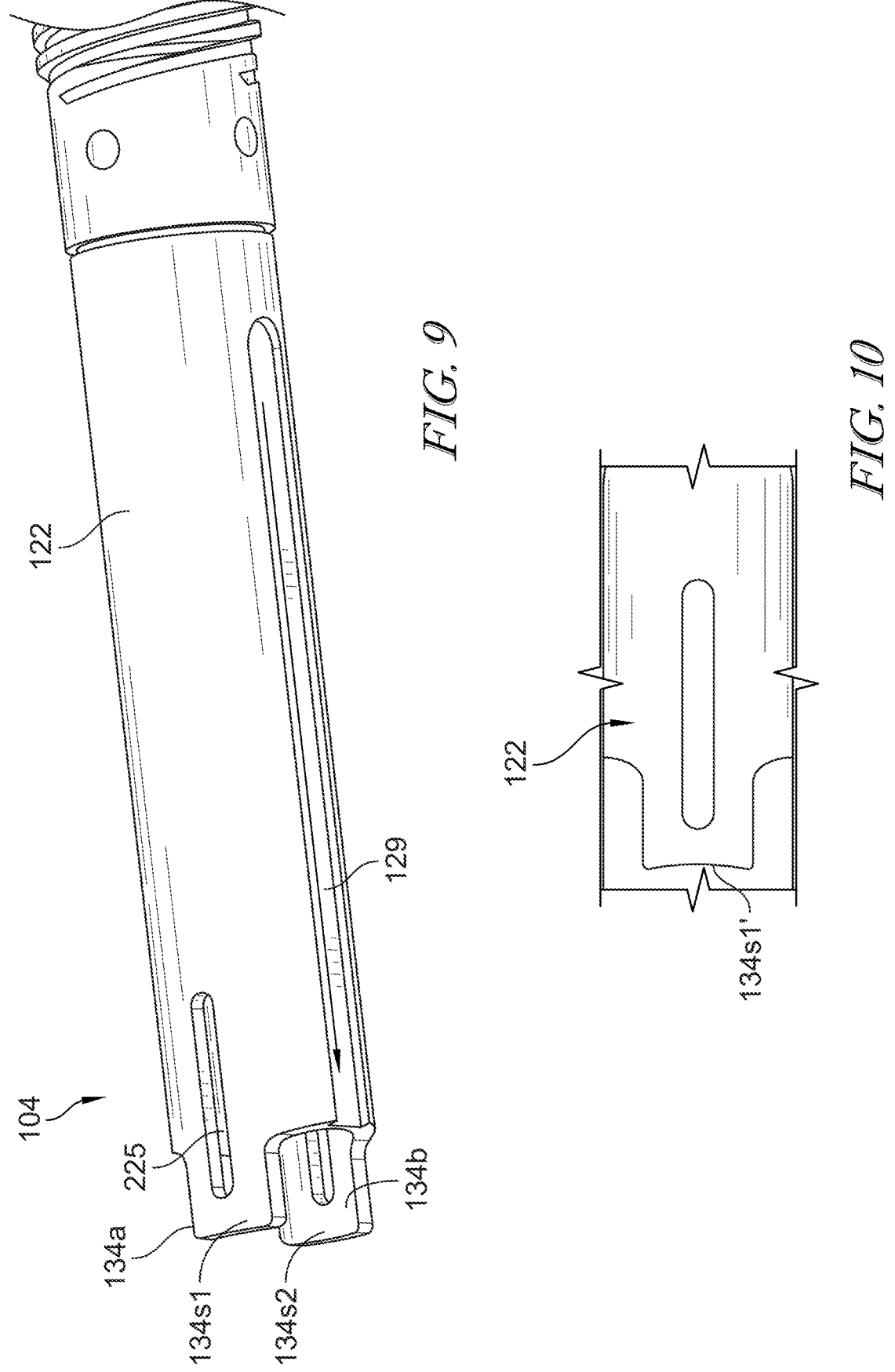
FIG. 9 is a detail view of a distal portion of an inner sleeve of the instrument of FIG. 1A.
FIG. 10 is a detail view of a distal portion of one embodiment of an inner sleeve of a combination derotation and reducer instrument.

The arms 134 can include distal contact surfaces 134s1, 134s2, as shown in FIGS. 1B and 9, which can be configured to abut and/or otherwise engage the spinal rod during reduction of the instrument 100 to advance the spinal rod distally into the bone anchor 10. In some embodiments, the distal translating portion 122 can taper distally towards substantially flat distal contact surfaces 134s1, 134s2. In some embodiments, however, other distal contact surface shapes can be utilized. For example, in some embodiments, the distal contact surfaces 134s1, 134s2 of the arms 134a, 134b can be shaped to match a rod shape with which the inner sleeve 104 is to be used. FIG. 10 illustrates one embodiment of such an arm with a curved contact surface 134s1'. The arms 134 can be rotationally offset from the extensions 112a, 112b of the instrument 100, such that the arms 134a, 134b can advance distally towards the bone anchor 10 when the inner sleeve 104 is advanced through the intermediate sleeve 102 without interfering with the engagement between the arms 116 and the bone anchor 10. Though two arms 134a, 134b are shown, the inner sleeve 104 can include any number of rod-engaging arms.

Figure 11:
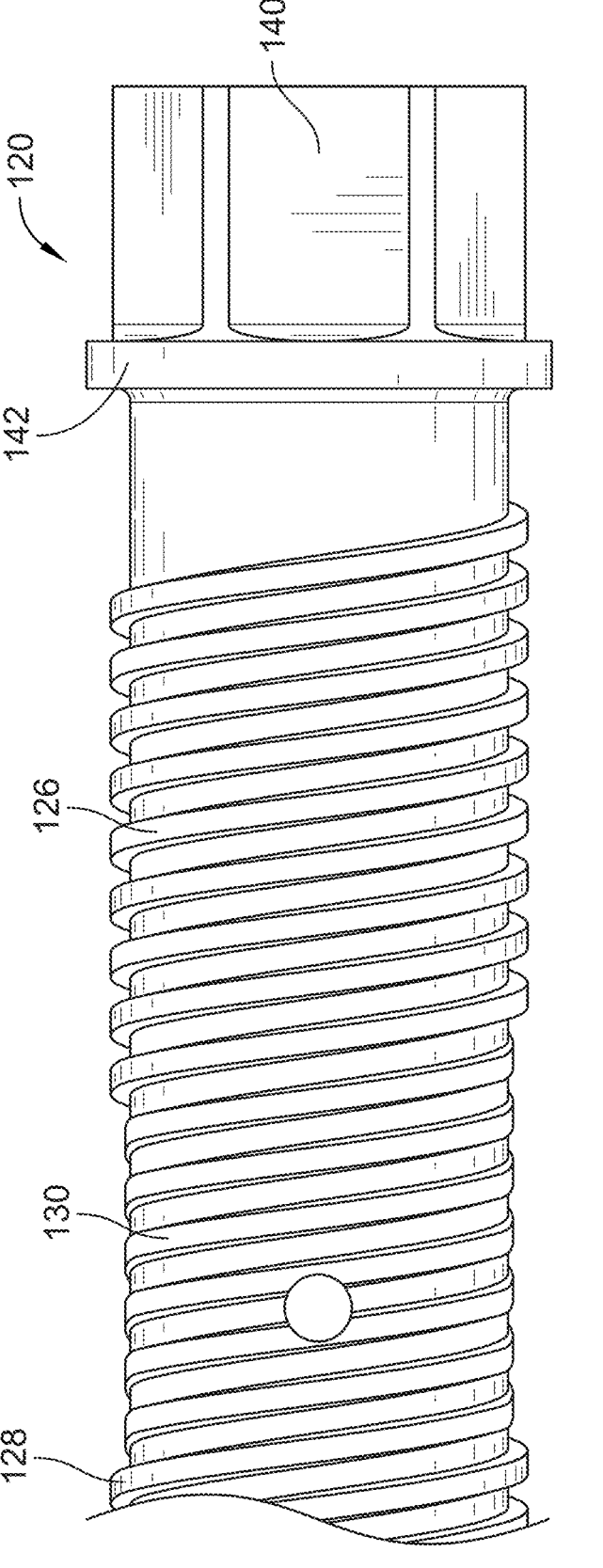
FIG. 11 is a detail view of a proximal portion of one embodiment of an inner sleeve of a combination derotation and reducer instrument.

The proximal threaded portion 120 can include one or more threaded portions formed thereon, as shown in FIG. 1B. For example, the proximal threaded portion 120 can include an exterior thread 126 configured to mate a counterpart threaded surface of the intermediate sleeve 102. The exterior thread 126 can be disposed along a length of the proximal portion 120. In some embodiments, the proximal threaded portion 120 can include a plurality of threaded portions formed thereon, as shown in FIG. 11. For example, the proximal threaded portion 120 can include a first threaded portion 126 and a second, additional distal threaded portion 128, which can prevent the threaded proximal portion 120 from being removed proximally out of the intermediate sleeve 102 unintentionally, while still enabling complete disassembly from the intermediate sleeve 102 when desired, e.g., for cleaning, etc. The first and second threaded portions 126, 128 can be separated by a non-threaded portion 130. In some embodiments, the first and second threaded portions 126, 128 and non-threaded portion 130 can be created by forming one continuous threaded portion and then removing the threads in one area to form the non-threaded portion 130. In some embodiments, the threads in the area of the non-threaded portion 130 can be left partially intact, as shown in FIG. 11, but reduced in depth to the point where they no longer engage with the threaded surface of the intermediate shaft 102. The presence of the non-threaded portion 130 can allow feedback to a user that they have retracted the inner sleeve 104 subassembly or reducing shaft to a maximum extent, as the inner sleeve 104 will translate freely relative to intermediate sleeve 102 once the threaded portion 126 is disengaged. To fully disassemble the inner sleeve 104 from the intermediate sleeve 102, however, a user will have to both pull proximally to translate the inner sleeve 104 and rotate to engage the second threaded portion 128 with the threaded inner surface of the intermediate shaft 102. Only once the second threaded portion 128 is fully disengaged from the intermediate sleeve 102 by threading proximally relative to the intermediate sleeve can the inner sleeve 104 be completely removed from the intermediate sleeve. That is, removal of the inner sleeve 104 relative to the intermediate sleeve 102 can be performed with a pulling force as well as a rotation, which can prevent unwanted back out of the inner sleeve 104 from the intermediate sleeve 102.

The threaded proximal portion 120 can include a modular drive interface 140 to facilitate application of torque or other forces to the inner sleeve 104, e.g., for advancing the reducer shaft along threads of the intermediate sleeve 102 during rod reduction. The drive interface 140 can have any geometry that facilitates application of torque or other forces to the inner sleeve 104, such as a hex drive as shown. The drive interface 140 can be received in or otherwise coupled to an instrument to impart a driving force onto the threaded proximal portion 120. The drive interface 140 can include a shoulder 142 (or groove or other similar feature) to facilitate mating of the inner sleeve 104 to other instruments, as described further below. In some embodiments, the drive interface can have a diameter that is about the same as a diameter of the inner sleeve 104, such that the drive interface does not substantially increase a diameter of the instrument 100 when a drive handle, powered driver, or other instrument is not coupled thereto.

A length of the inner sleeve 104 can vary. In some embodiments, the inner sleeve 104 can be provided in different lengths to facilitate different amounts of axial reduction. For example, the inner sleeve 104 can be configured to provide axial reduction of about 20 mm, about 40 mm, and about 60 mm in certain embodiments by varying the length thereof. Use of certain lengths can be preferred in different environments, for example, use of a short inner sleeve 104 can prevent proximal crowding at lordotic/concave segments or can be especially useful in pediatric applications where space is limited.

Figure 12A:
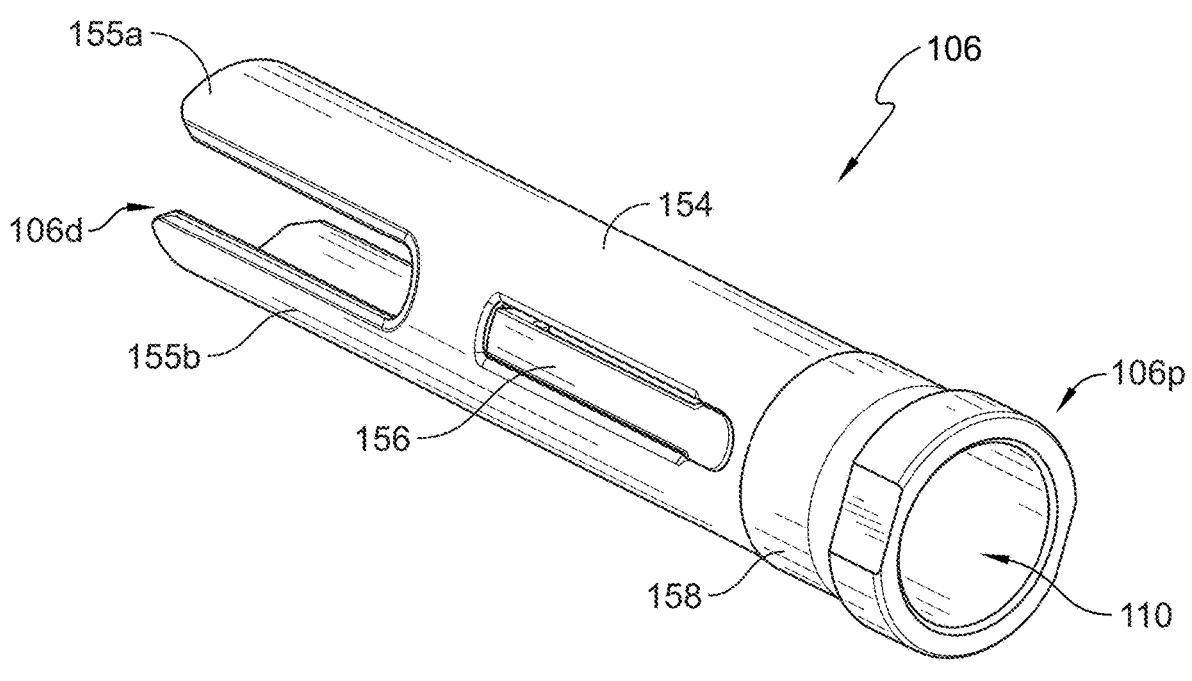
FIG. 12A is a perspective view an outer sleeve of the instrument of FIG. 1A.
Figure 12B:
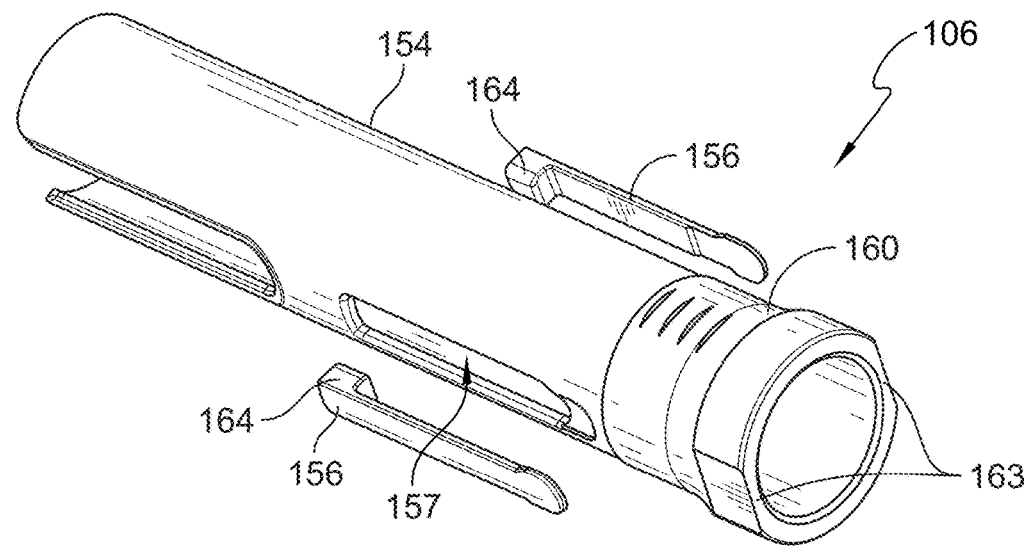
FIG. 12B is an exploded view of the outer sleeve of FIG. 12A.

As discussed above, the outer sleeve 106 be coupled to the intermediate sleeve 102 of the instrument 100 to aid in locking the instrument 100 to a bone anchor 10 or other implant. FIGS. 12A-12B illustrate one embodiment of the outer sleeve 106 that can be coupled to the intermediate sleeve 102. The outer sleeve 106 can include a tubular shaft 154 that defines the inner channel 110 passing therethrough and terminates at a distal end with opposed extensions 155a, 155b. As shown in FIGS. 1A-1E, the tubular shaft 154 can be sized to receive the intermediate sleeve 102 therethrough. The outer sleeve 106 can include one or more movable arms 156 for engaging with the intermediate sleeve 102, as discussed above. As shown, the movable arms 156 can be received in a pair of recesses or cavities 157 formed in the tubular shaft 154 of the outer sleeve 106 to pass into the inner channel 110 to engage the intermediate sleeve 102 disposed therein. The movable arms 156 can be formed in a similar manner as the movable arms 116 of the intermediate sleeve 102, e.g., as integrally formed portions of the sleeve that are partially cut and have a living hinge, or as separate components that can be affixed to the outer sleeve shaft 154, e.g., using welding, adhesives, mechanical fasteners, etc. In some configurations of the instrument 100, e.g., the closed configuration discussed with respect to FIG. 13C below, the movable arms 156 can align with the grooves 135 formed in the intermediate sleeve 102 such that the movable arms 156 can pass into the lumen 110 and into the grooves 135.

The outer sleeve 106 can include a proximal portion 158 that can include one or more features to facilitate gripping the outer sleeve 106 and imparting force thereto. For example, the proximal portion 158 can include one or more grooves, ridges, or other surfaces 160 to facilitate a user grasping the outer sleeve 106 during use. Additionally or alternatively, the proximal portion 158 can include other surface features to facilitate the application of force to the outer sleeve, such as one or more flats 163 disposed around a circumference of the outer sleeve.

The movable arms 156 can engage the intermediate sleeve 102 disposed within the outer sleeve 106. As shown, the movable arms 156 can include a protrusion 164 at a distal end thereof and can be coupled to the outer sleeve 106 at a proximal end thereof. In a resting position where the radially outward surfaces of the arms 156 are flush with the outer surface of the outer sleeve 106, the protrusions 164 can extend into the inner channel 110. During use, the movable arms can be deflected radially outward and return radially inward depending on interactions of the protrusions 164 with the grooves 135 formed in the intermediate sleeve 102 that can be disposed within the inner channel 110 of the outer sleeve 106.

Figures 13A, 13B:
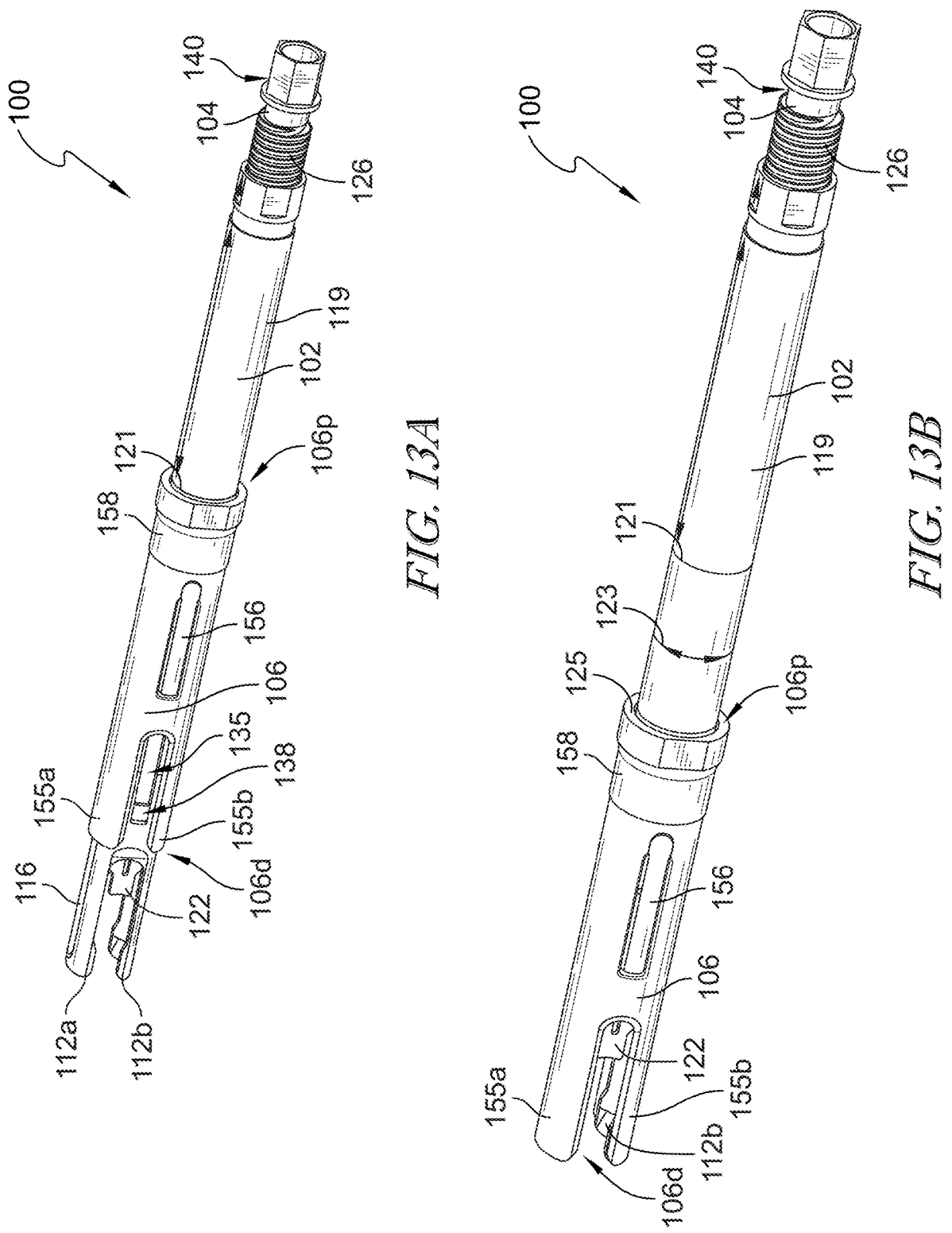
FIG. 13A is a perspective view of the instrument of FIG. 1A in a configuration where the outer sleeve is retracted proximally.
FIG. 13B is a perspective view of the instrument of FIG. 1A in a second configuration where the outer sleeve is advanced distally.
Figure 13C:
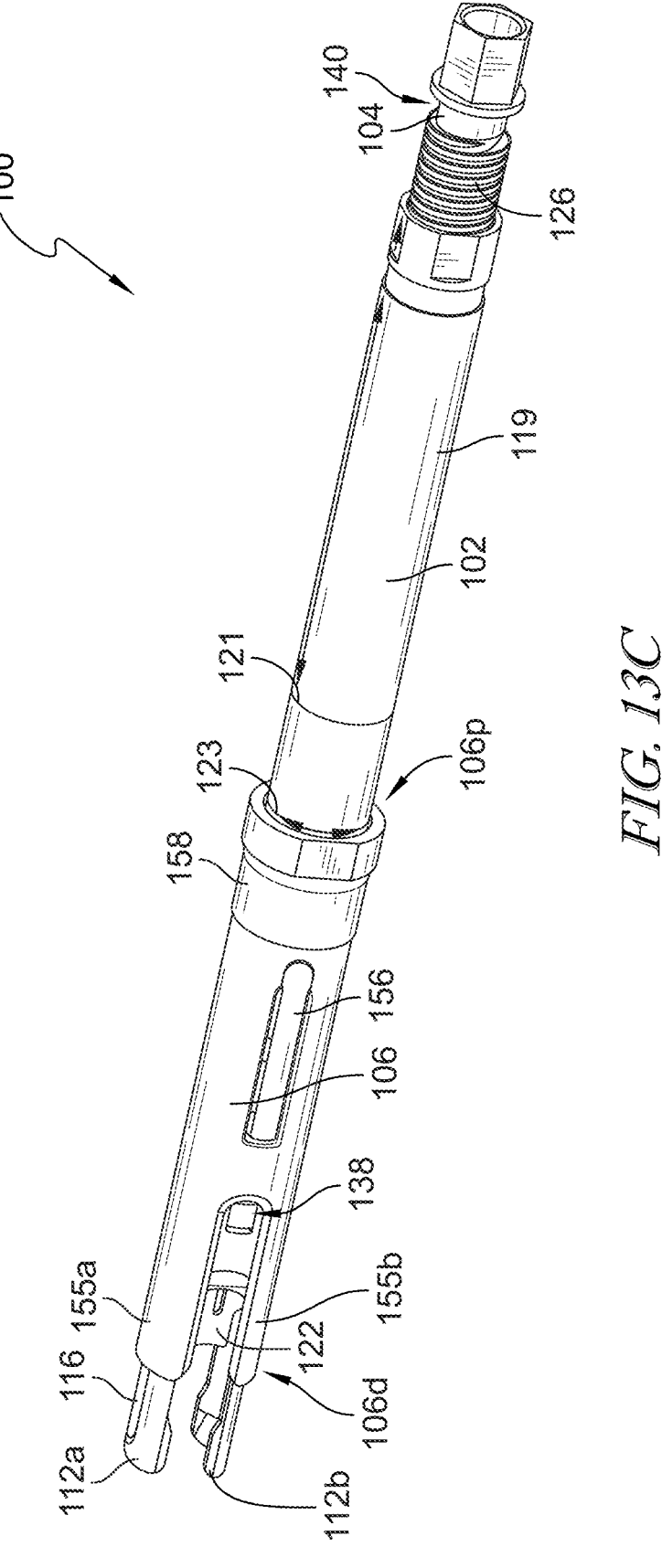
FIG. 13C is a perspective view of the instrument of FIG. 1A in a third configuration where the outer sleeve is at an intermediate state between the configurations of FIGS. 13A and 13B.

FIGS. 13A-13C illustrate certain operational aspects of the instrument 100. FIG. 13A illustrates the instrument 100 in an open configuration wherein the outer sleeve 106 is proximally retracted relative to the intermediate sleeve 102. In such a configuration, the distal extensions 155a, 155b of the outer sleeve 106 can be retracted proximally to expose the distal extensions 112a, 112b of the intermediate sleeve 102 and, in particular, the movable arm 116 formed in each extension 112. In such a configuration, the movable arm 116 of each extension 112 of the intermediate sleeve 102 can deflect radially outward when an implant, such as the bone anchor 10, passes between the extensions 112a, 112b and forces the movable arms 116 outward. In addition, the protrusions 164 formed on the movable arms 156 of the outer sleeve 106 can be disposed within a proximal detents 136 of the grooves 135, meaning the position of the outer sleeve 106 relative to the intermediate sleeve 102 is stable and a force will be required to move the outer sleeve 106 distally. Further, a user can receive feedback of the position of the outer sleeve 106 relative to the intermediate sleeve 102. The feedback can be haptic because a user can feel the protrusions 164 of the movable arms 156 seat into the proximal detent 136 of the groove 135 when withdrawing the outer sleeve 106 proximally relative to the intermediate sleeve 102. The feedback can also be visual because a proximal end of the outer sleeve 106 can align with a marking, such as a proximal line 121, formed on the intermediate sleeve 102.

In the configuration of FIG. 13A, the instrument 100 can quickly connect to a bone anchor 10 by moving the intermediate sleeve 102 over the receiver member 12 of the bone anchor 10 such that the receiver member 12 passes into the inner channel 108 of the intermediate sleeve 102 and between the distal extensions 112a, 112b of the intermediate sleeve 102.

To lock the instrument 100 against separation from the bone anchor 10, the outer sleeve 106 can be advanced distally from the configuration of FIG. 13A to the configuration of FIG. 13B after the intermediate sleeve 102 is coupled to the bone anchor 10. Advancing the outer sleeve 106 distally relative to the intermediate sleeve 102 can cause the distal extensions 155a, 155b of the outer sleeve 106 to cover the distal extensions 112a, 112b of the intermediate sleeve 102 and, in particular, the movable arm 116 formed in each extension 112. In such a configuration, the movable arm 116 of each extension 112 of the intermediate sleeve 102 can be prevented from deflecting radially outward, which would be required to separate the intermediate sleeve 102 from the bone anchor 10.

In addition, distally advancing the outer sleeve 106 relative to the intermediate sleeve 102 can cause the protrusions 164 of the movable arms 156 of the outer sleeve 106 to deflect radially outward as the protrusions exit the proximal detents 136 and travel distally through the central channels 139 of the grooves 135. When the outer sleeve 106 reaches a distally advanced position of FIG. 13B, the protrusions 164 of the movable arms 156 of the outer sleeve 106 can move radially inward to seat within the distal detents 138 of the grooves 135. This action of the movable arms 156 can create haptic feedback to a user that the outer sleeve 106 is fully advanced. Further, visual feedback can also be provided when the proximal end of the outer sleeve 106 aligns with a marking, such as a distal line 125, formed on the intermediate sleeve 102. Once in the closed or locked configuration of FIG. 13B, there is a rigid and secure coupling formed between the instrument 100 and the bone anchor 10, such that the instrument 100 can be utilized for rod reduction, derotation, or other operations where forces are imparted to the bone anchor and/or the vertebra it is implanted in via the instrument 100.

The outer sleeve 106 can be separated from the intermediate sleeve 102 for cleaning, etc. FIG. 13C illustrates the outer sleeve 106 in an intermediate state between the proximally retracted configuration of FIG. 13A and the distally advanced configuration of FIG. 13B. In the intermediate state of FIG. 13C, the outer sleeve can be positioned such that the protrusions 164 of the movable arms 156 of the outer sleeve 106 are positioned near a midpoint of the grooves 135 of the intermediate sleeve 102. Visual feedback of the correct position can be provided to a user when a proximal end of the outer sleeve 106 is aligned with an intermediate line 123 on the intermediate sleeve 102. In such a configuration, a user can rotate the outer sleeve 106 relative to the intermediate sleeve 102. During rotation, the protrusions 164 can exit the central channels 139 of the grooves 135 by deflecting radially outward and riding up the ramped sidewalls or chamfered edges 141 of the grooves 135 at this position. The protrusions 164 can then travel along an outer surface of the intermediate sleeve 102 as the outer sleeve 106 is separated from the intermediate sleeve 102. In view of the configuration of the grooves 135 with proximal and distal detents 136, 138, the outer sleeve 106 can be biased to toward the distally advanced or proximally retracted configurations of FIGS. 13A and 13B, and positioning the outer sleeve 106 in the intermediate position of FIG. 13C that allows disassembly can require intentional manipulation of the instrument 100.

A length of the outer sleeve 106 can vary. For example, in some embodiments, a length of the outer sleeve 106 can be smaller than that of the intermediate sleeve 102 to allow one or more devices to be coupled to a proximal portion 119 of the intermediate sleeve 102. Example devices that can be coupled to the proximal portion 119 of the intermediate sleeve 102 can include a frame or rack to facilitate derotation maneuvers, a counter-torque device, a modular handle, an inserter, a navigation system element, or the like. The intermediate sleeve 102 can therefore be used to manipulate one or more a vertebrae or other bones. For example, the intermediate sleeve 102 can facilitate application of derotation, distraction, compression, or other forces to a vertebra or to a fixation construct, e.g., to correct a spinal angle, deformity, or other condition of the patient. The instrument can be configured in manner where such couplings are not impeded by the outer sleeve 106, even when the outer sleeve 106 is disposed in its proximally retracted configuration because, in such a configuration, the proximal end of the outer sleeve 106 aligns with the proximal line 121, which can be positioned distal to the proximal portion 119 utilized for such couplings.

Figure 14:
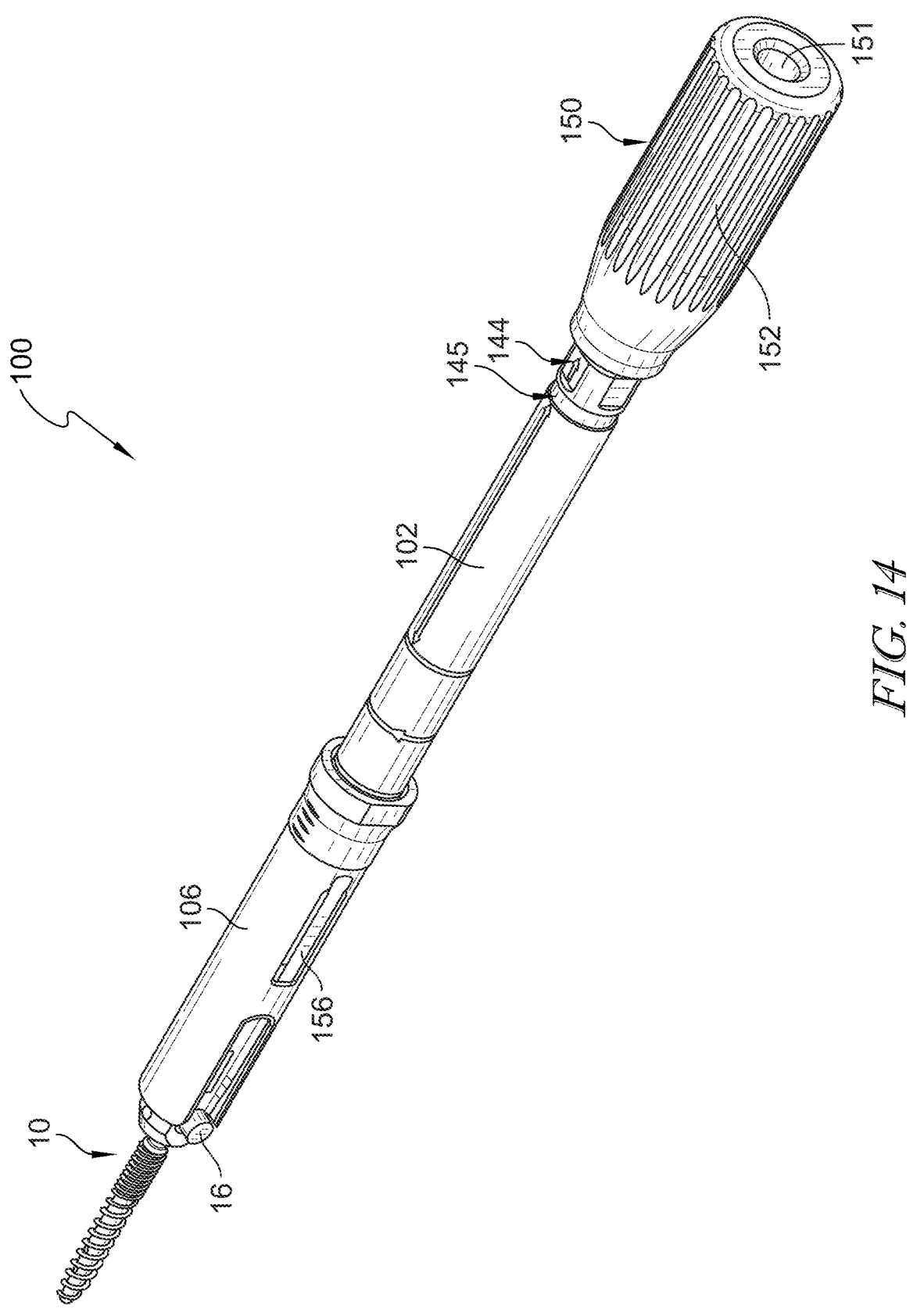
FIG. 14 is a perspective view of one embodiment of a handle coupled to the instrument of FIG. 1A.

One or more devices can be coupled to the instrument 100. FIG. 14 illustrates one embodiment of a handle or adapter 150 coupled to the instrument 100. The drive interface 140 of the inner sleeve 104 can have any geometry that facilitates application of torque or other forces to the inner sleeve 104, such as the illustrated hex drive of FIGS. 1A-1E and 11. In some embodiments, the handle 150 can include gripping surfaces 152 to facilitate grasping thereof, such as ribs, knurling, grooves, protrusions, recesses, etc. The handle 150 can engage the drive interface 140 via a corresponding hex drive to facilitate distal advancement of the inner sleeve 104 relative to the intermediate sleeve 102 via relative rotation of these components.

The handle 150 of FIG. 14 is modular and can be separated from the inner sleeve 104 when not in use. This can be advantageous because it can allow of the selective use of the handle when desired, or the use of other drivers, such as a drill or other powered driver, a tool like a wrench for increasing leverage, etc. The ability to selectively remove the handle can also clear the area around the proximal end of the instrument 100 to provide for easier working in a crowded surgical site where multiple instruments may be disposed near one another, and can facilitate easier coupling of other accessories, such as a derotation frame or rack, etc.

In some embodiments, the handle 150 can be configured to slide over a proximal end of the inner sleeve 104 without any features to prevent removal thereof, i.e., axial separation of the handle from the inner sleeve. In other embodiments, the handle 150 can include one or more retention features to help maintain the position of the handle relative to the inner sleeve 104 until a deliberate action is taken to separate the two components. The one or more retention features can be passive or active in nature. For example, a passive retention feature can include one or more balls disposed in the handle 150 that can be seated in one or more detents formed on the inner sleeve 104 such that, once engaged, the cooperation of the balls and detents can resist separation of the handle from the inner sleeve until a sufficient amount of force is applied. An example active retention feature can include a latch that can positively lock the handle 150 to the inner sleeve 104 until a user takes deliberate action to release the latch and separate the two components. In one embodiment, for example, the handle 150 can include a latch that can interface with a feature formed on the proximal end of the inner sleeve 104, such as the shoulder 142, to prevent axial separation of the two components until a user releases the latch.

Figure 15:
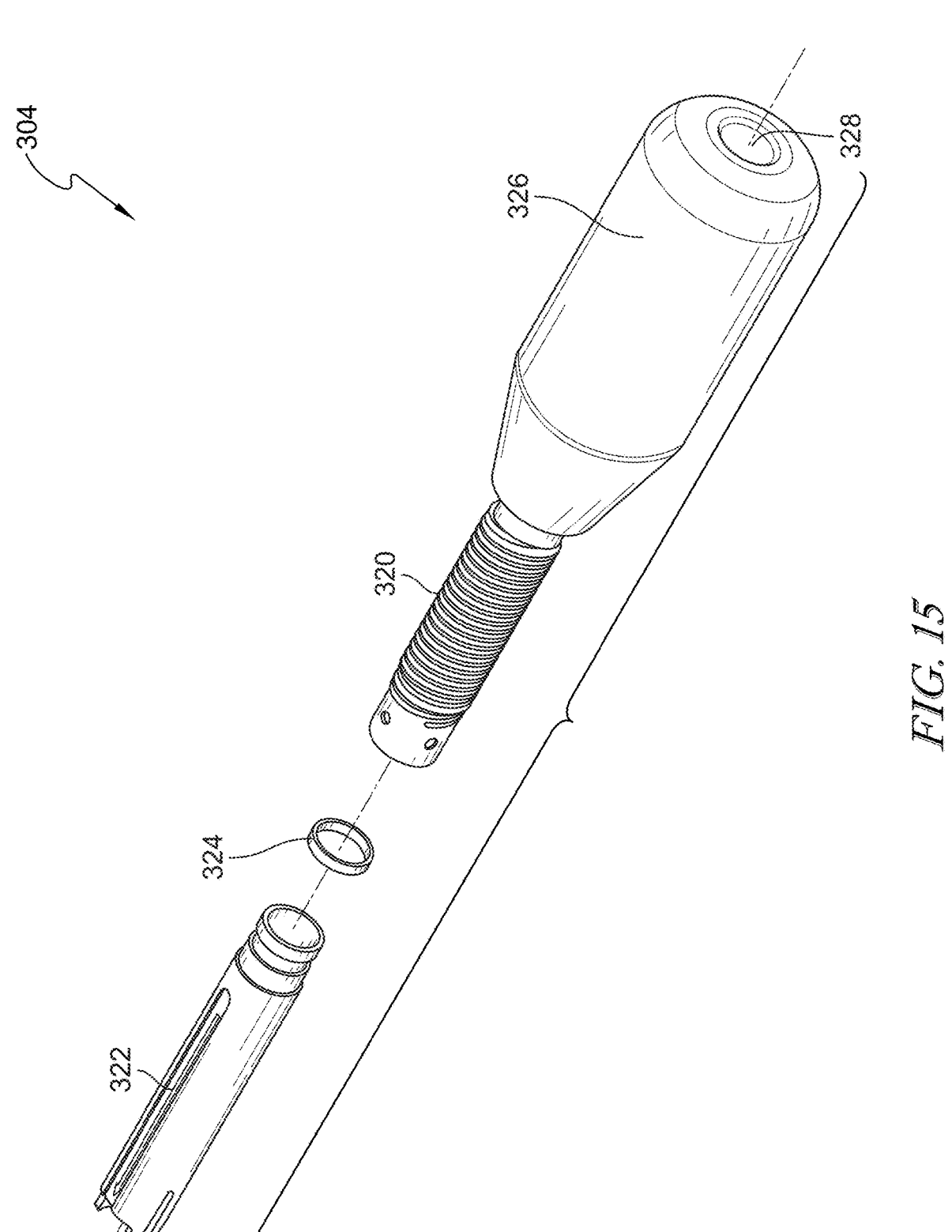
FIG. 15 is an exploded view of one embodiment of an inner sleeve with integrated handle.

FIG. 15 illustrates an alternate embodiment of an inner sleeve 304 with an integrated handle 326. The inner sleeve 304 can include a threaded proximal portion 320, a translating distal portion 322, and a washer 324, e.g., a thrust washer that can separate and serve as a bearing surface between the translating distal portion 322 and threaded proximal portion 320. As shown, the inner sleeve 304 can include an integrated handle 326 at a proximal end of the threaded proximal portion 320. The handle 326 can be integrally formed with the threaded proximal portion 320 to provide a unitary structure. The structure can be formed in a monolithic manner from a single piece of material or can be formed from multiple separate components rigidly coupled to one another to form a single unitary structure. The handle 326 can be configured to be grasped by a user to rotate the threaded proximal portion 320. In this manner, the integrated handle 326 can be a substitute for the modular drive feature 140 (e.g., flats, hex drive feature, etc.) of the reducer instrument 100 to allow direct manipulation of the inner sleeve 304 without the need for any additional instrumentation. As noted above, any of a variety of handle configurations or other structures can be coupled with the threaded proximal portion in any of a variety of modular or permanent manners. These can include use of modular coupling features, such as the hex-drive feature 140, integrally formed structures, such as the integrated handle 326 and threaded proximal portion 320, and other coupling methods, such as joining components with a setscrew or other mechanical fastener, adhering components, welding components, etc.

In addition, the handle 326 can include a lumen 328 extending therethrough to allow introduction of a setscrew or other instrument to a bone anchor coupled to a reducer instrument. The lumen 328 can extend through the integrated handle 326 and threaded proximal portion 320. In embodiments where a modular handle 150 is utilized, it can include a lumen 151 as well that, when coupled to the threaded proximal portion 120 of the inner sleeve 104, can align with the inner channel 133 of the threaded proximal portion to permit introduction of a setscrew or other instrument therethrough. Accordingly, the methods described herein can be utilized with embodiments including both a modularly coupled handle and an integrally formed and/or permanently coupled handle.

In use, an instrument 100 can be assembled by coupling the various components to one another. For example, the intermediate sleeve 102 can be inserted into the inner channel 110 of the outer sleeve 106 and positioned such that the movable arms 156, and more specifically the protrusions 164 formed at distal ends thereof, fall into the grooves 135 formed on the intermediate sleeve 102. The outer sleeve 106 can then be moved proximally relative to the intermediate sleeve 102 to the unlocked or proximally retracted position that readies the assembly for coupling with a bone anchor 10 or other implant. In addition, the inner sleeve 104 can be inserted into the inner channel 108 of the intermediate sleeve, though it is also possible to perform this step of assembly after coupling the intermediate sleeve 102 to a bone anchor or other implant first, and/or securing the coupling by advancing the outer sleeve 106 relative to the intermediate sleeve to the locked or distally advanced position where the extensions 155a, 155b of the outer sleeve cover the extensions 112a, 112b of the intermediate sleeve and prevent radially outward movement of the arms 116 of the intermediate sleeve 102.

When inserting the inner sleeve 104 into the intermediate sleeve 102, the longitudinal groove 129 of the distal translating portion 122 can be aligned with the one or more pins 131 on the inner surface of the intermediate sleeve 102, such that the pins enter the grooves 129 and thereby prevent relative rotation between the distal translating portion and the intermediate sleeve as the two components translate relative to one another. Further, the proximal threaded portion 120 can be rotated to engage threads 126 (or the multiple threaded portions 126, 128 as shown in FIG. 11) with threads 132 formed on an inner surface of the intermediate sleeve 102. Once assembled, e.g., as shown in FIG.

13A, the threaded proximal portion 120 of the inner sleeve 104 can extend proximally from the intermediate sleeve 102 while the translating distal portion 122 of the inner sleeve remains disposed therein for distal advancement towards the extensions 112a, 112b of the intermediate sleeve as the threaded proximal portion 120 is rotated relative to the intermediate sleeve 102.

Use of an at least partially assembled instrument 100 can include positioning the instrument 100 over a rod 16 and adjacent to a bone anchor or pedicle screw 10. The instrument can be in an unlocked configuration wherein the outer sleeve 106 is retracted proximally relative to the intermediate sleeve 102, thereby allowing deflection or movement of the arms 116 of the intermediate sleeve. The spinal rod 16 can be disposed between the extensions 112a, 112b of the intermediate sleeve 102 while the receiver member 12 is disposed distal to the intermediate sleeve 102. The intermediate sleeve 102 can be advanced towards the bone anchor 10 to engage a notch thereof. The instrument 100 can be advanced distally to first pass over and capture the rod 16 between the extensions 112a, 112b, followed by an approach to the bone anchor 10. In other embodiments, however, the instrument 100 can be coupled to the bone anchor prior to rod placement. In such embodiments, the rod can be introduced into the space between the extensions 112a, 112b laterally.

The instrument 100 can engage the receiver member 12 of the bone anchor 10. During engagement, the extensions 112a, 112b of the intermediate sleeve 102 can pass over the receiver member 12 and distal protrusions of the movable arms 116 can make contact with the receiver member 12 and be urged radially outward at their distal ends. Once the intermediate sleeve 102 has sufficiently advanced over the receiver member 12 and the distal ends of the movable arms 116 are aligned with a groove or notch 18 formed in an outer surface of the receiver member 12, the distal ends of the movable arms 116 can return radially inwards toward the receiver member to click into place (e.g., as a result of a biasing force, such as their tendency to return to a state where an outer surface of each arm 116 is flush with an outer surface of the intermediate sleeve 102 and a protrusion at a distal end of each arm 116 extends into the inner channel 108 between the extensions 112a, 112b).

Once the movable arms 116 engage with the notch 18 of the receiver head 12, the instrument 100 can be provisionally coupled to the bone anchor 10 or other implant. To secure the coupling against inadvertent removal and ensure rigidity between the two components, the outer sleeve 106 can be advanced distally toward the distal end of the intermediate sleeve 102 and the bone anchor 10. As the outer sleeve 106 advances distally, the extensions 155a, 155b can slide over and cover the extensions 112a, 112b of the intermediate sleeve 102, which can block the movable arms 116 against any movement of deflection radially outward relative to the intermediate sleeve 102. This can effectively lock the instrument 100 to the bone anchor 10 in a manner that provides a rigid coupling capable of enduring both axial forces, as might be experienced during rod reduction using the inner sleeve 102, as well as non-axial forces, as might be experienced when utilizing the instrument 100 to perform derotation or other maneuvers to correct spinal abnormalities.

The above-described process for assembling the instrument 100 and/or coupling the intermediate sleeve 102 of the instrument to a bone anchor can be performed in a variety of orders, allowing flexibility for different surgical workflows that can enhance efficiency and accommodate different user preferences. For example, assembly of the intermediate and outer sleeve components of the instrument 100 can be performed at a "back table" or surgical prep area before passing the assembled instrument to a surgeon for use. Further, the inner sleeve 104 can be assembled at this time or later. In addition, a bone anchor can be coupled to the intermediate sleeve 102 before or after implantation in a patient and/or before or after assembly of the intermediate sleeve 102 and the inner sleeve 104.

In certain embodiments, for example, the intermediate sleeve 102 can be coupled to a bone anchor 10 prior to implanting the bone anchor into a patient and the bone anchor can be implanted using an instrument that passes through the intermediate sleeve to couple with the implantable shank 14 of the bone anchor. This can be done with or without the inner sleeve 104 being coupled to the intermediate sleeve 102. In embodiments where a bone anchor 10 is implanted with the intermediate sleeve 102 coupled thereto and without the inner sleeve 104, the inner sleeve can be coupled to the intermediate sleeve after the bone anchor is implanted and the driver instrument is removed from the intermediate sleeve.

The flexibility of assembly can permit, for example, a workflow in which the instrument 100 is coupled to a bone anchor 10 and a driver instrument at a "back table" or surgical prep area. The assembly can then be passed to a surgeon or other user ready for use to implant the bone anchor in the patient. Following implantation, the driver instrument can be removed, leaving the instrument 100 coupled to the implanted bone anchor and ready for use in reducing a rod using the inner sleeve 104. In embodiments where the intermediate sleeve 102 is coupled to a bone anchor prior to implantation or otherwise prior to rod placement generally proximate to the bone anchor, the rod can later be placed by passing it laterally through the rod slot opening of the intermediate sleeve 102 between the extensions 112a, 112b.

Once the instrument 100 is assembled, including the outer sleeve 106, intermediate sleeve 102, and inner sleeve 104, and the instrument is coupled to a bone anchor 10 with a rod 16 passing between the extensions 112a, 112b of the intermediate sleeve, a rotation force can be applied to the threaded proximal portion 120 of the inner sleeve 104 to advance the translating distal portion 122 towards the spinal rod. The threaded proximal portion 120 of the inner sleeve 104 can rotate while the translating distal portion 122 advances in a distal motion to allow the static arms 134a, 134b of the distal translating portion 122 to engage the spinal rod 16 and urge it distally toward the bone anchor 10.

Figures 8A, 8B:
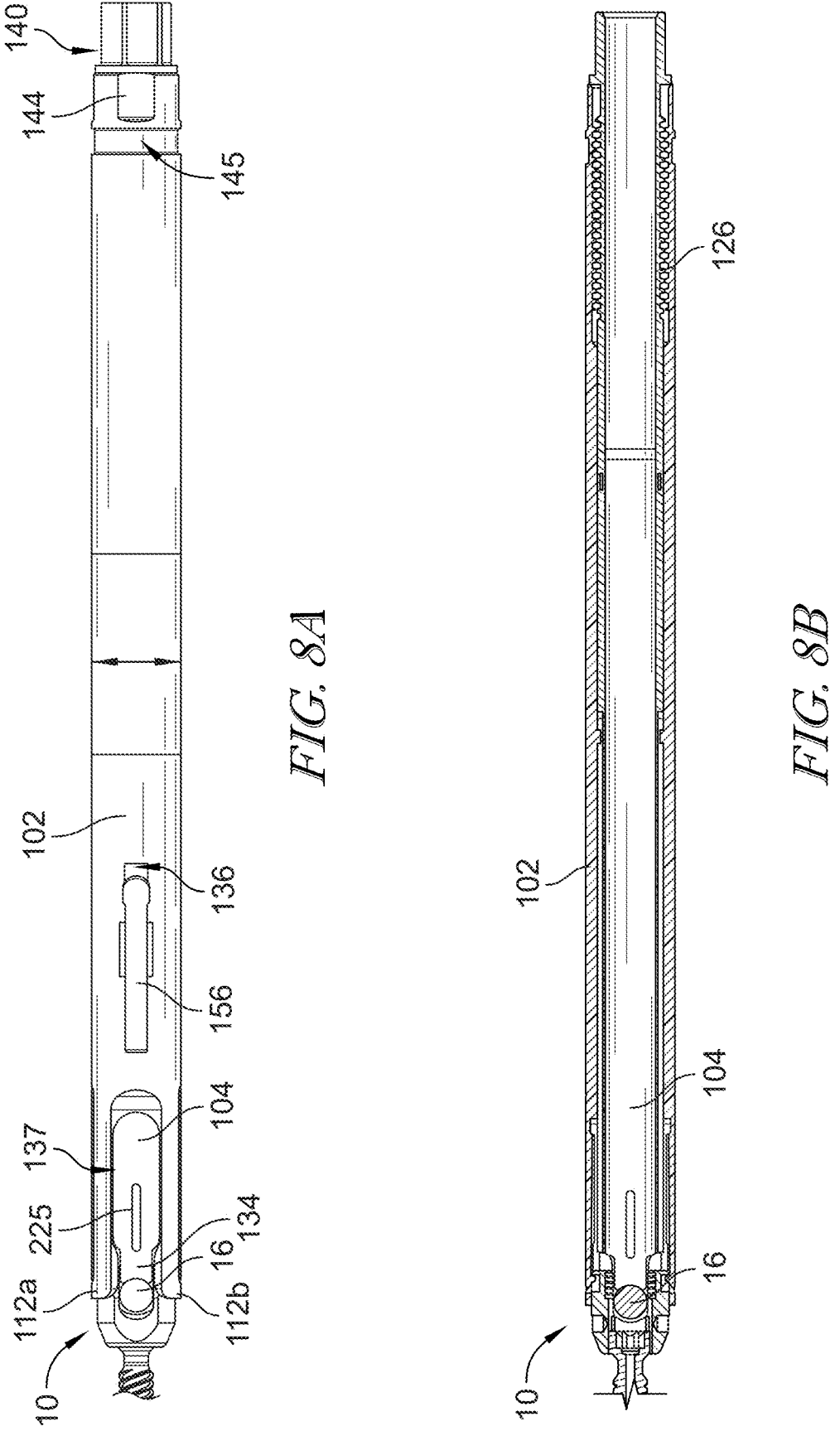
FIG. 8A is a side view of an inner sleeve disposed within an intermediate sleeve of the instrument of FIG. 1A.
FIG. 8B is a longitudinal cross-sectional view of the components of FIG. 8A.
Figures 8C, 8D:
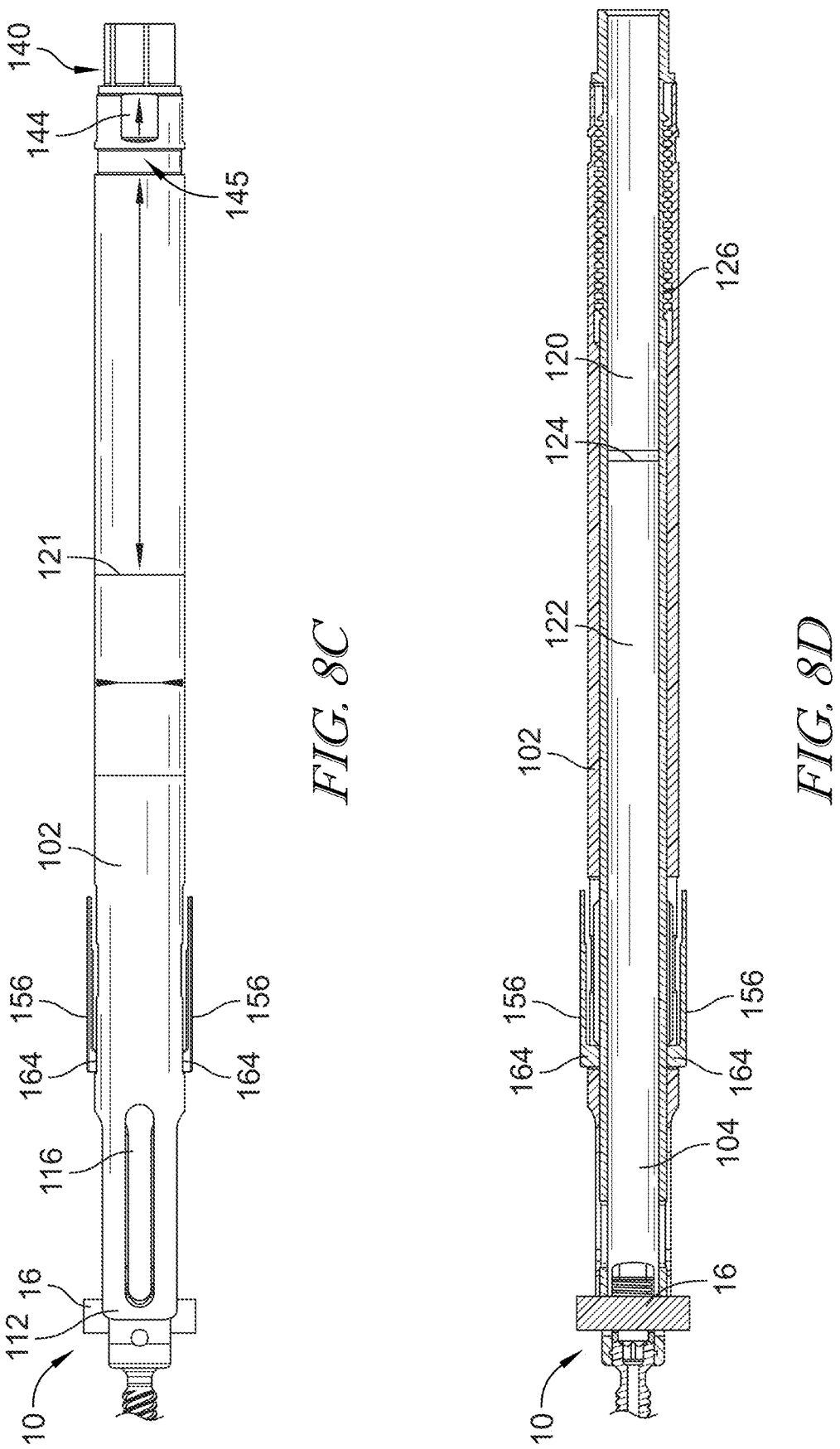
FIG. 8C is an alternative side view of the components of FIG. 8A.
FIG. 8D is an alternative longitudinal cross-sectional view of the components of FIG. 8A.

The shoulder 142 (see FIG. 11) formed on the proximal translating portion 120 of the inner sleeve 104 can abut the intermediate sleeve 102 (as shown in FIGS. 8A and 8B) when the threaded proximal portion 120 is at a distal-most position and cannot proceed distally. In this configuration, the spinal rod 16 is reduced within the bone anchor 10.

In addition to rod reduction, a user can impart forces to the instrument 100 to perform derotation of a vertebra coupled thereto. The implantation of the bone anchor 10 in the vertebra, in combination with the rigid coupling of the instrument 100 to the bone anchor 10 when in the locked configuration in which the outer sleeve 106 is advanced distally relative to the intermediate sleeve 102, can effectively transfer forces applied to the instrument 100 to the vertebra. A surgeon or other user can utilize any combination of positioning maneuvers, such as derotation, etc., and rod reduction via rotation of the inner sleeve 104 relative to the intermediate sleeve 102, in order to perform the desired procedure.

In connection with the above-noted steps of rod insertion/ capture, vertebra positioning, and rod reduction, a user can secure the rod 16 relative to the bone anchor 10 using a setscrew that can be inserted through the inner channel 133 in the inner sleeve 104 and threaded into the bone anchor receiver member 12 using an inserter instrument. In some embodiments, an instrument for inserting a setscrew or other closure mechanism can be passed through the inner channel 133 of the inner sleeve 104, with or without a setscrew loaded therein, to apply the setscrew to the receiver member 12 of the bone anchor 10. The setscrew can be advanced distally through the inner sleeve 104, e.g., through the threaded proximal portion 120 and the translating distal portion 122, to engage the spinal rod 16 to lock the spinal rod to the bone anchor 10. In some embodiments, the inserter instrument can be used to provisionally tighten the setscrew to the bone anchor by the application of a rotational force, and tightening can be done in incremental steps, potentially interspersed with various other operations, such as derotation, distraction, or other positioning changes to one or more vertebra. Further, in some embodiments, a derotation maneuver and/or a distraction maneuver can be performed using the inserter instrument when disposed through the inner sleeve 104 to introduce and drive the setscrew. This can be in addition to, or in place of, performing such derotation and/or distraction maneuvers using the instrument 100 without any inserter present.

Figure 17:
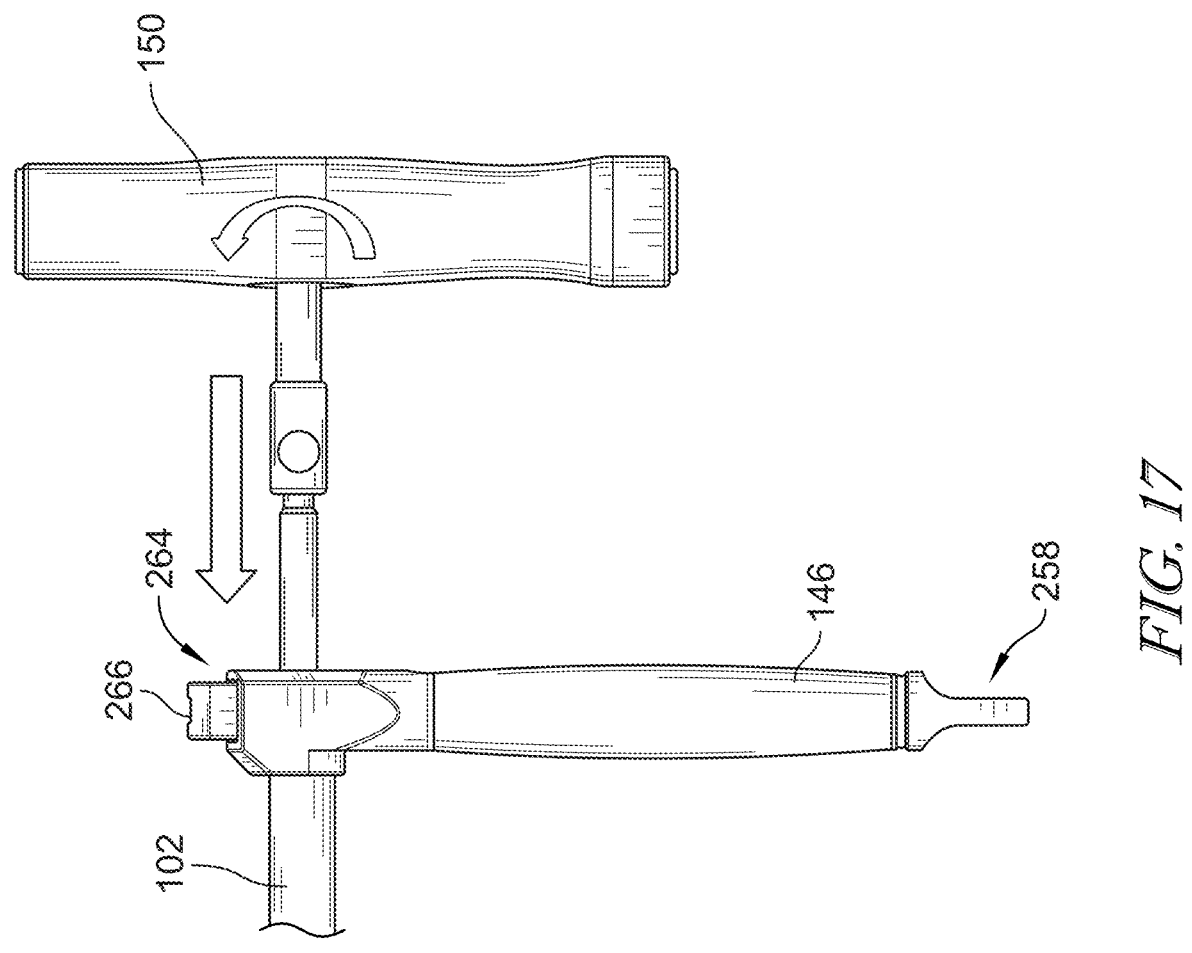
FIG. 17 is a side view of one embodiment of a driver introduced through an inner sleeve disposed within the intermediate sleeve of FIG. 16.
Figure 16:
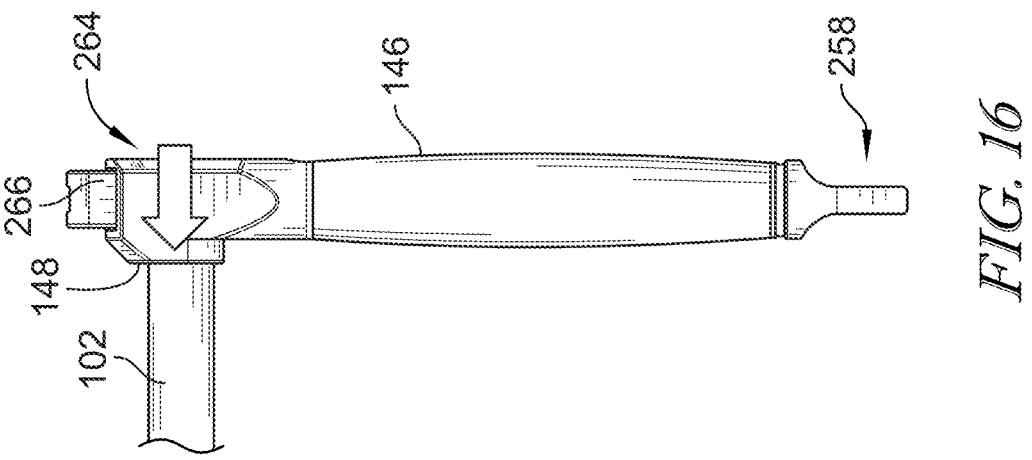
FIG. 16 is a side view of one embodiment of a counter-torque device disposed on an intermediate sleeve of the instrument of FIG. 1A.
Figure 26:
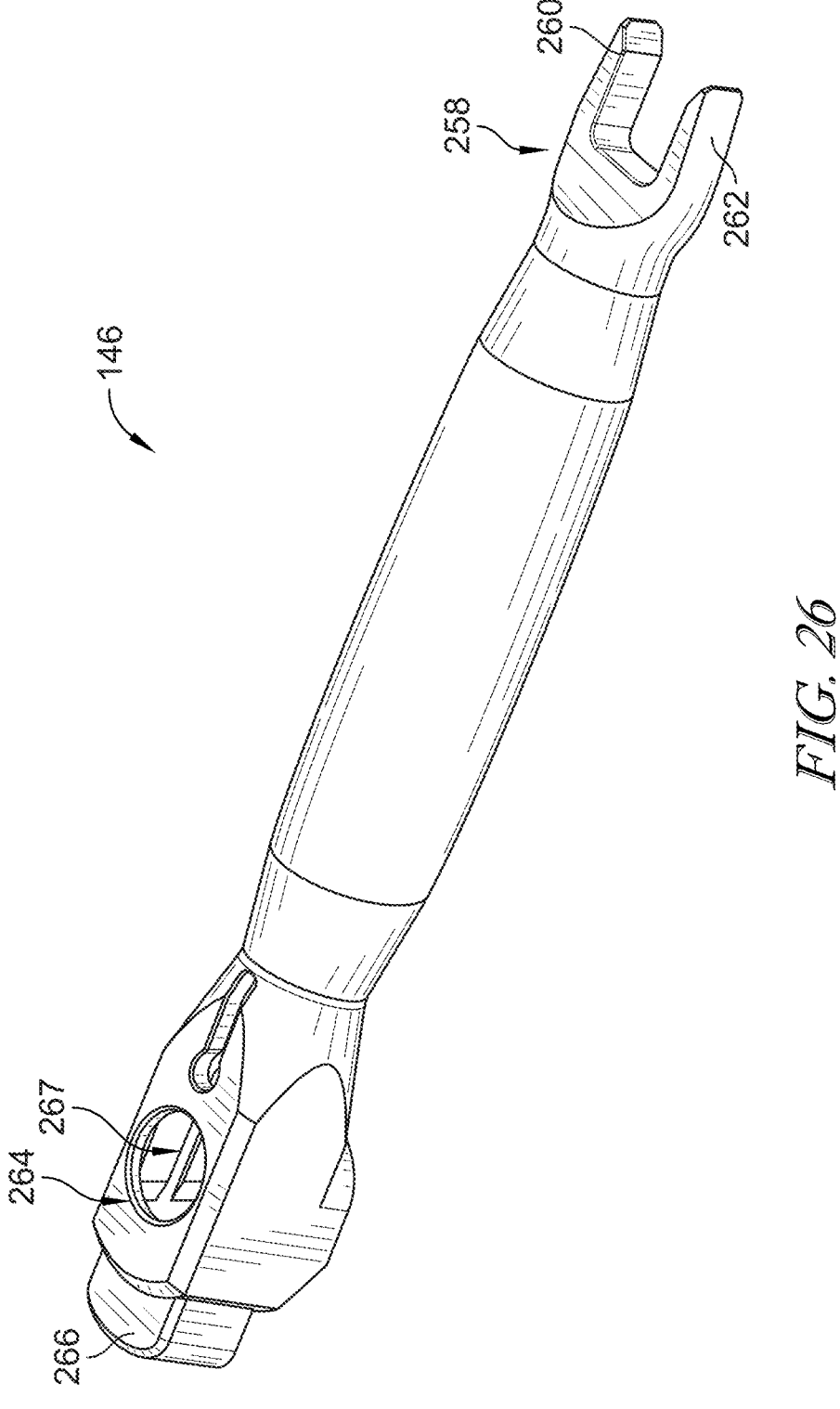
FIG. 26 is a perspective view of the modular counter-torque instrument of FIG. 24.
Figure 27:
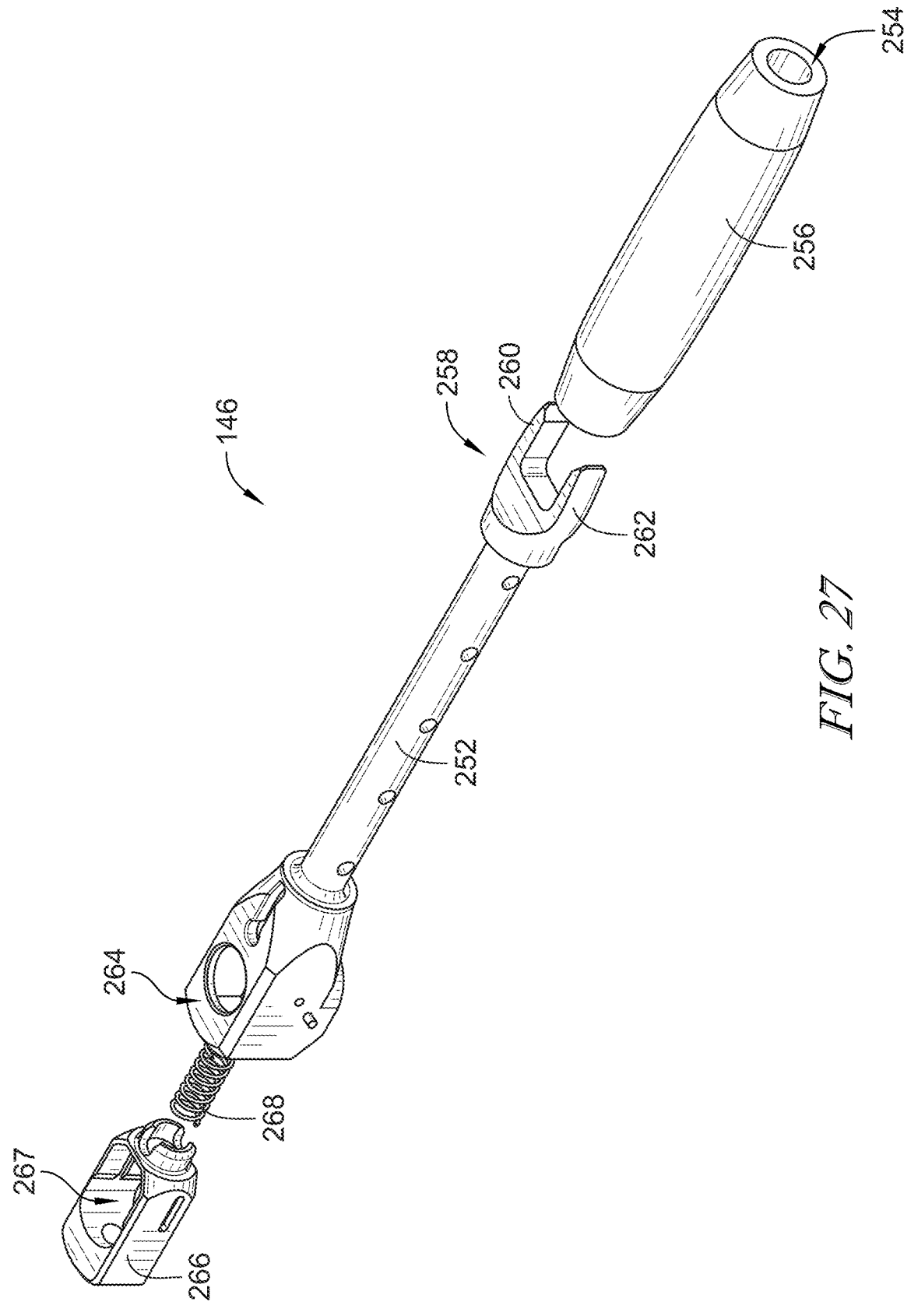
FIG. 27 is an exploded view of the modular counter-torque instrument of FIG. 26.

Final tightening of a setscrew can require the application of counter-torque given the forces involved. FIG. 16 illustrates a counter-torque device 146 disposed on the intermediate sleeve 102. The counter-torque device 146 can couple to the proximal flats 144 and the groove 145 on the intermediate sleeve 102 to form a positive connection therewith that prevents relative rotation between the components. The proximal flats 144 can be spaced in a manner that allows a corresponding mating feature 148 of the counter-torque device 146 to couple in multiple orientations (e.g., the flats can be formed in a hex or other pattern around a circumference of the instrument to allow coupling at a variety of rotational orientations relative to the instrument). As shown in FIG. 17, a driver 150 can be introduced through the inner sleeve 104 to engage a setscrew and perform tightening with the aid of the counter-torque device 146 that locks the rod within the receiver member of the anchor. Note that FIGS. 16 and 17 illustrate the counter-torque device 146 coupled to the intermediate sleeve 102 via a first end having a housing 264 with a spring-loaded coupler 266. This can provide positive engagement that secures the counter-torque device 146 to the intermediate sleeve 102 to prevent separation of the two components. In some embodiments, however, the counter-torque device 146 can be coupled to the intermediate sleeve 102 via a slip-fit of a second, forked end 258 against the flats 144 of the intermediate sleeve 102. As described in more detail below, FIGS. 26 and 27 illustrate the counter-torque device 146 and the forked end 258.

Figures 18, 19:
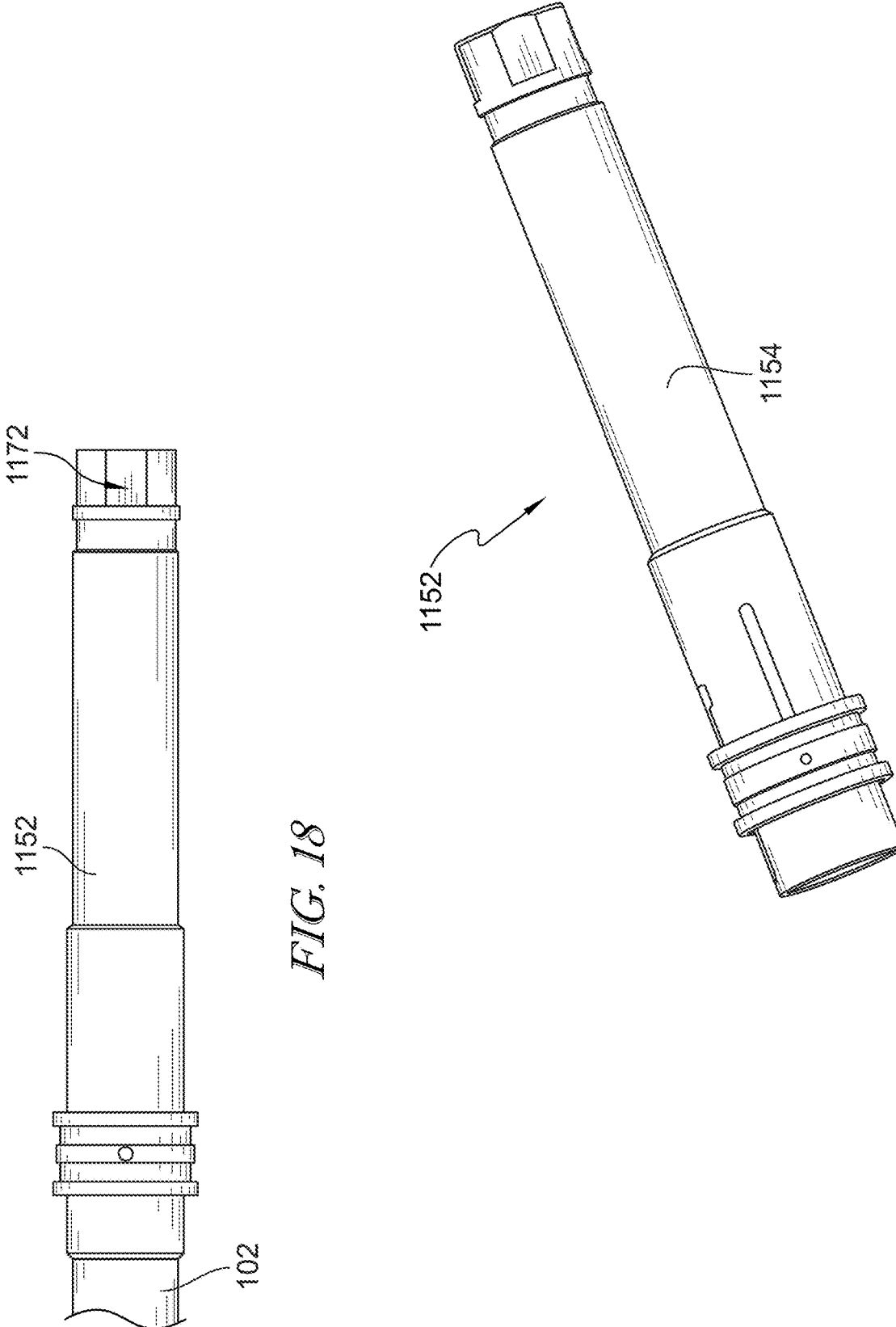
FIG. 18 is a side view of one embodiment of a modular extension sleeve coupled to an intermediate sleeve of the instrument of FIG. 1A.
FIG. 19 is a perspective view of the modular extension sleeve of FIG. 18.

In addition, if further proximal extension of the instrument 100 is required for derotation maneuvers, etc., a modular extension sleeve or tube 1152 can be utilized to couple with the intermediate sleeve 102 of the instrument 100. Directly engaging the flats of the intermediate sleeve 102 can allow the application of counter-torque directly through the extension sleeve 1152 via connection to the same type of modular counter-torque device 146 shown in FIGS. 16 and 17. This is in contrast to other devices that provide coupling through an inner threaded sleeve component. FIG. 18 illustrates a modular extension sleeve 1152 coupled to a proximal end of an intermediate sleeve 102 of an instrument 100.

Figures 20, 21:
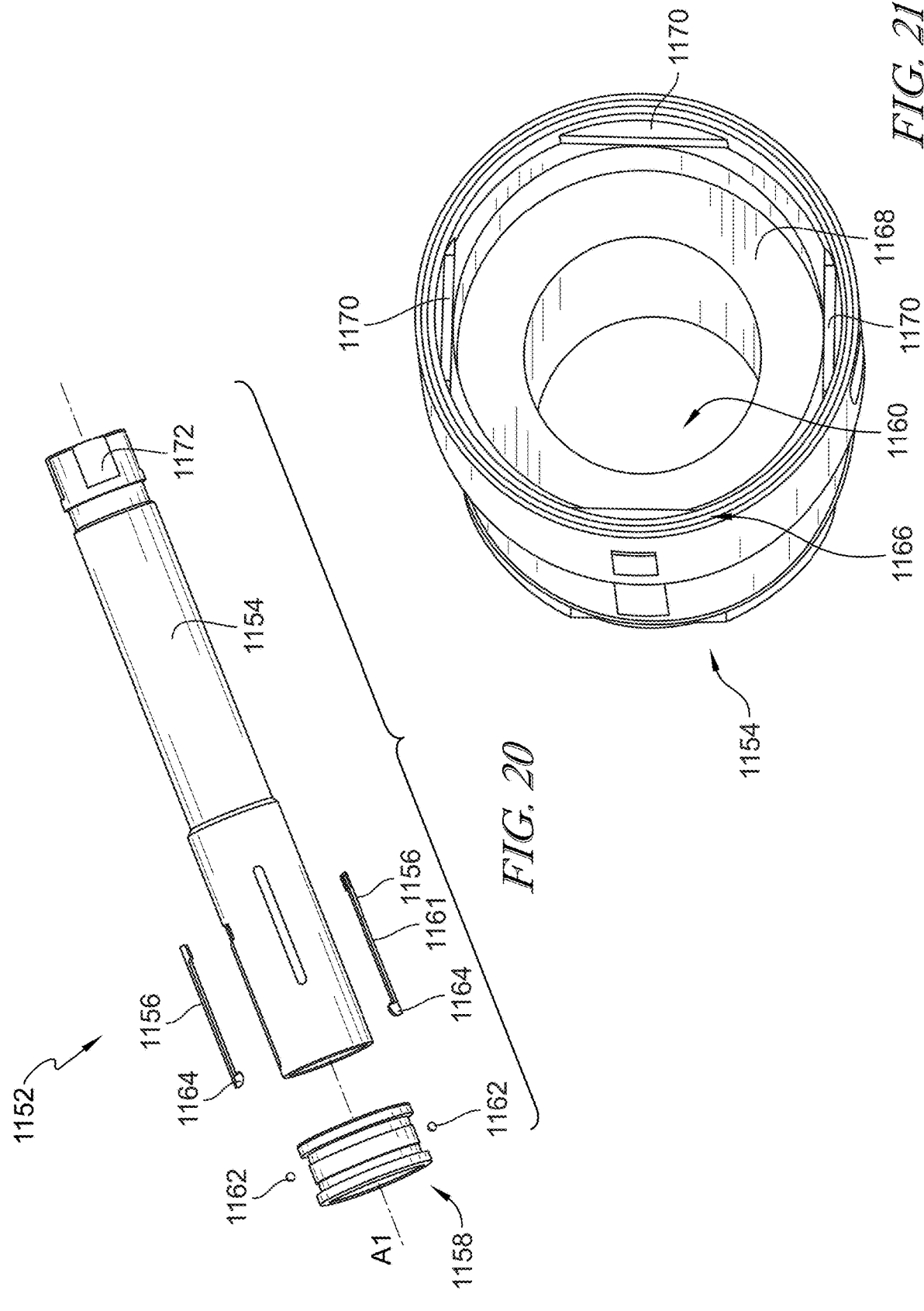
FIG. 20 is an exploded view of the modular extension sleeve of FIG. 19.
FIG. 21 is a distal perspective view of a tubular shaft of the modular extension sleeve of FIG. 19.

FIGS. 19-21 illustrate an extension sleeve 1152 that can be coupled to the intermediate sleeve 102 in greater detail. The extension sleeve 1152 can be used to provide additional leverage when manipulating a vertebra or other bone to which the sleeve is coupled. For example, the extension sleeve 1152 can facilitate application of derotation, distraction, compression, or other forces to a vertebra or to a fixation construct, e.g., to correct a spinal angle, deformity, or other condition of the patient. The extension sleeve can also provide an attachment point for a derotation rack, navigation system, or other surgical instrumentation. Because these functions are also provided by the intermediate sleeve 102 and instrument 100, the sleeve 1152 can serve as an extension in cases where additional length is needed.

The extension sleeve 1152 can include a tubular shaft 1154 having one or more movable arms 1156 for engaging with the instrument 100 to secure the extension sleeve 1152 thereto. The extension sleeve 1152 can include a locking ring 1158 for selectively maintaining the arms 1156 in engagement with the instrument 100. The sleeve 1152 can include an interior sidewall that defines an inner channel 1160. The locking ring 1158 can be disposed around an outer surface of the sleeve 1152 to move axially relative thereto. The locking ring 1158 can be coupled to the sleeve 1152 via one or more pins 1162 inserted therethrough.

The movable arms 1156 can be configured to grasp a drive interface of an instrument inserted therethrough. The movable arms 1156 can be movable between an open configuration in which an instrument can be inserted and removed from the extension sleeve 1152 and a closed position in which an instrument is captured or retained within the extension sleeve. The locking ring 1158 can be disposed in an unlocked position in which the movable arms 1156 are free to move, or pivot, relative to the tubular shaft 1154, and a locked position in which the movable arms 1156 are constrained from moving relative to the tubular shaft 1154. The movable arms 1156 can pivot radially inward and/or radially outward relative to a longitudinal axis A1.

The movable arms 1156 can include a body 1161 having a protrusion 1164 at a distal end thereof. The body 1161 can be pivoted radially inward to bring the protrusion 1164 into the lumen 1160 to grasp an instrument or other object inserted therethrough. The locking ring 1158 can axially slide over the movable arms 1156 to move the arms from the open configuration to the closed configuration and/or to prevent the arms 1156 from moving relative to the sleeve 1152, thereby locking the arms in the closed configuration.

The extension sleeve 1152 can include a distal drive interface 1166 configured to mate with the proximal flats on the intermediate sleeve 102. Tools inserted through the drive interface 1166 can pass through at least a portion of the lumen 1160, and tools inserted through the lumen 1160 can pass through at least a portion of the drive interface 1166. The drive interface 1166 and the lumen 1160 can be separated by an abutment surface or shoulder 1168 that is defined by an interior sidewall of the extension sleeve 1152 to prevent an instrument inserted into the drive interface 1166 from advancing too far proximally into the lumen 1160.

A proximal end of the extension sleeve 1152 can include flats 1172 that resemble those formed on the intermediate sleeve 102, thereby enabling connection of the same modular handle to both subassemblies, and therefore the application of counter-torque to both subassemblies via the same handle. In some embodiments, a length of the proximal end portion of the extension sleeve 1152 including the flats 1172 can be extended to provide a larger surface area for engagement by various instruments that couple thereto.

Figures 22, 23:
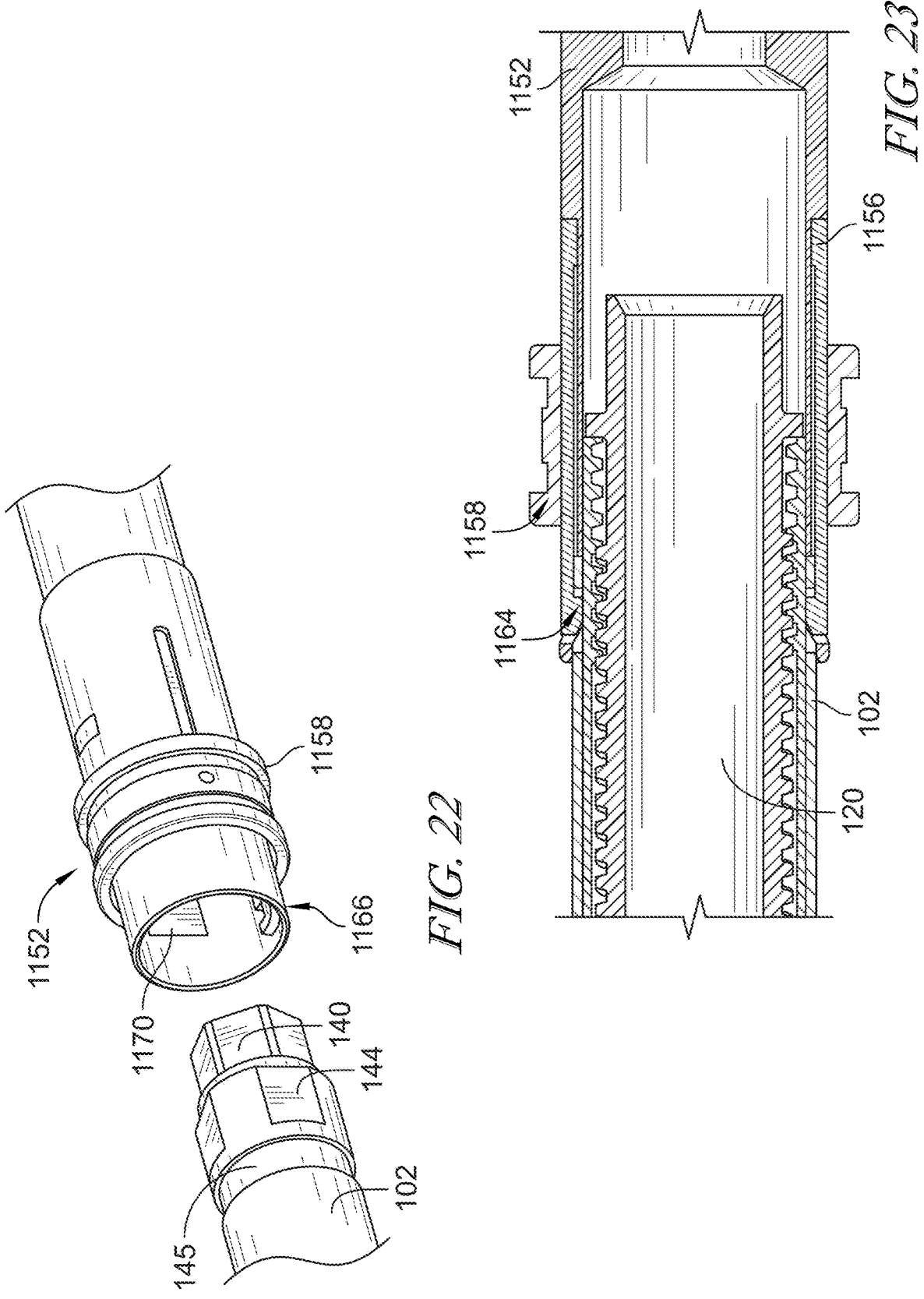
FIG. 22 is a perspective view of coupling between the modular extension sleeve of FIG. 19 and an intermediate sleeve of the instrument of FIG. 1A.
FIG. 23 is a longitudinal cross-sectional view of a coupling between the intermediate sleeve and modular extension sleeve of FIG. 22.

FIG. 22 illustrates the extension sleeve 1152 coupling to the intermediate sleeve 102 while bypassing the threaded proximal portion 120 of the inner sleeve 104. For example, the extension sleeve 502 can include one or more engagement surfaces 1170 positioned in the drive interface 1166 or lumen 1160. As shown, the engagement surfaces 1170 can protrude at various angles from an interior surface of the extension sleeve 1152 to engage the proximal flats 144 formed on the intermediate sleeve 102. In this manner, the extension sleeve 1152 can make a positive connection with the intermediate sleeve 102 while the threaded proximal portion 120 of the inner sleeve 104 remains disposed in the channel of the extension sleeve 1152 without engagement from the extension sleeve 1152. As a result, the extension sleeve 1152 can remain fixed relative to the intermediate sleeve 102 and can be capable of exerting derotating forces on the vertebra without rotating relative thereto. As shown in FIG. 21, the abutment surfaces 1170 can be positioned at roughly 90-degree angles relative to one another to abut the flats to facilitate coupling and restrict rotation of the extension sleeve 1152 relative to the intermediate sleeve 102. In other embodiments, however, fewer or additional abutment surfaces 1170 can be employed and spaced around a circumference of the sleeve 1152, with corresponding flats 144 disposed around a circumference of the intermediate sleeve 102.

Figure 25:
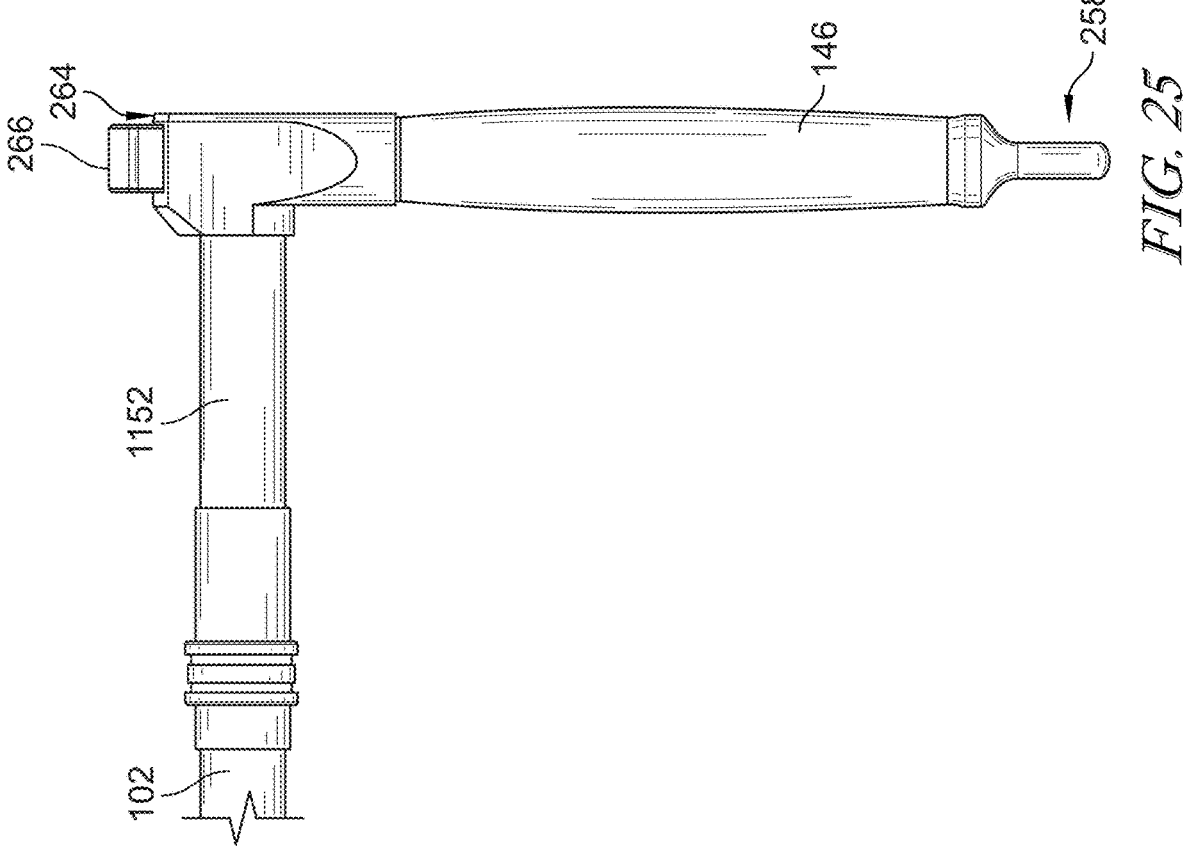
FIG. 25 is a side view of the modular counter-torque instrument of FIG. 24 coupled to the modular extension sleeve of FIG. 19 that is, in turn, coupled to an intermediate sleeve of the instrument of FIG. 1A.
Figure 24:
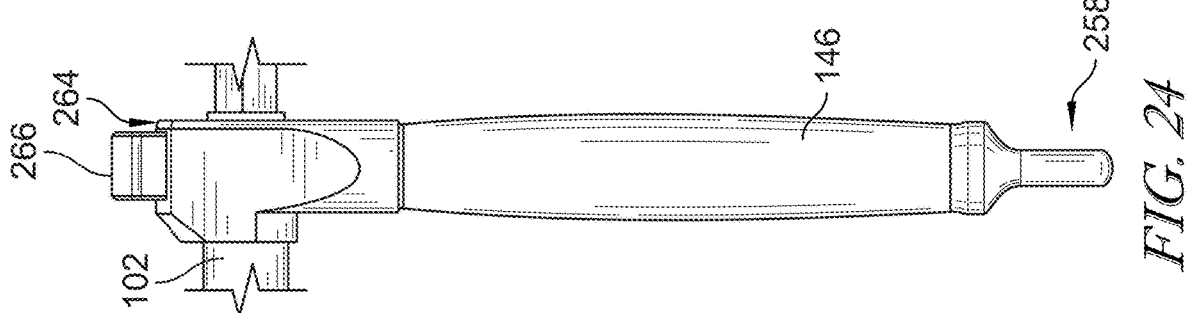
FIG. 24 is a side view of one embodiment of a modular counter-torque instrument coupled to an intermediate sleeve of the instrument of FIG. 1A.

FIG. 23 illustrates a cross-sectional view of a coupling between the intermediate sleeve 102 and the extension sleeve 1152. As discussed above, retention of the extension sleeve 1152 can be achieved via the locking ring 1158 that constrains the movable arms 1156 that engage the circumferential groove 145 on the intermediate sleeve 102. As noted above, the proximal end of the extension sleeve 1152 can include flats 1172 that resemble those formed on the intermediate sleeve 102, thereby enabling connection of the same modular handle to both subassemblies, and therefore the application of counter-torque to both subassemblies via the same handle. This can be seen, for example, in FIG. 24 where a modular counter-torque instrument 146 like that shown in FIGS. 16 and 17 is shown coupled to an intermediate sleeve 102 of an instrument 100 directly, as well as FIG. 25 where the counter-torque instrument 146 is shown coupled to a modular extension sleeve 1152 that is, in turn, coupled to the intermediate sleeve 102 of the instrument 100. Note that FIGS. 24 and 25 illustrate the counter-torque instrument 146 coupled to the intermediate sleeve 102 via a first end having a housing 264 with a spring-loaded coupler 266. This can provide positive engagement that secures the counter-torque instrument 146 to the intermediate sleeve 102 to prevent separation of the two components. In some embodiments, however, the counter-torque instrument 146 can be coupled to the intermediate sleeve 102 via a slip-fit of a second, forked end 258 against the flats 144 of the intermediate sleeve 102.

FIGS. 26 and 27 illustrate the counter-torque instrument 146 in greater detail. The counter-torque instrument 146 can include a shaft 252 disposed within a channel 254 of a handle 256. The handle 256 can include gripping features (e.g., knurling, ridges, recesses, finger loops, etc.) to facilitate a user grasping the handle during operation. The counter-torque instrument 146 can include one or more features for engaging the instrument 100 or extension sleeve 1152 to facilitate rotation of the inner sleeve 104 relative to the intermediate sleeve 102 by resisting any rotation of the intermediate sleeve along with the inner sleeve. For example, the counter-torque instrument 146 can terminate at one end with a fork 258 having prongs 260, 262. An opposite end of the counter-torque instrument 146 can include a housing 264 having a spring-loaded coupler 266 disposed therein. The coupler 266 can be moved relative to the housing 264 by exerting a force thereon that compresses a spring disposed within the housing 264. The coupler 266 can include a bore formed therein with one or more ridges formed around a partial circumference thereof.

In use, the coupler 266 can be pressed inward against the spring bias force and positioned over a proximal end of another component, such as the one or more proximal flats 144 of the intermediate sleeve 102 or the flats 1172 of the extension sleeve 1152. Once positioned, the coupler 266 can be allowed to move outward under the spring bias force such that the one or more ridges formed around a partial circumference of the bore engage a portion of the component disposed within the bore, such as the flats 144 of the intermediate sleeve 102 or the flats 1172 of the extension sleeve 1152. In such a configuration, the counter-torque instrument 146 can be prevented from rotating relative to the intermediate sleeve 102 and can therefore be utilized to impart counter-torque to the intermediate sleeve when rotating the inner sleeve 104. In addition, the coupler 266 can also interface with a groove or other feature of the intermediate sleeve 102 or extension sleeve 1152 to prevent unintended axial separation of the counter-torque instrument 146 from the captured component. For example, a portion of the coupler 266 can extend into the groove 145 formed on the intermediate sleeve 102 to prevent separation of the two components until a user depresses the coupler against the spring bias. Alternatively, and as noted above with regard to FIGS. 16, 17, 24, and 25, the forked end of the counter-torque instrument 146 can be used in a similar manner, i.e., by disposing the opposed forks 260, 262 against opposed flats 144 of the intermediate sleeve 102 or the flats 1172 of the extension sleeve 1152 in order to allow use of the counter-torque instrument 146 to provide counter-torque when rotating the inner sleeve 104.

Various devices and methods disclosed herein can be used in minimally invasive surgery and/or open surgery. While various devices and methods disclosed herein are generally described in the context of surgery on a human patient, the methods and devices disclosed herein can be used in any of a variety of surgical procedures with any human or animal subject, or in non-surgical procedures.

Various devices disclosed herein can be constructed from any of a variety of known materials. Example materials include those that are suitable for use in surgical applications, including metals such as stainless steel, titanium, titanium nitride, nickel, cobalt, chrome, cobalt-chromium, or alloys and combinations thereof, polymers such as PEEK, ceramics, carbon fiber, and so forth. The various components of the devices disclosed herein can be rigid or flexible. In addition, one or more of the components or devices disclosed herein can be formed as monolithic or unitary structures, e.g., formed from a single continuous material, or can be formed from separate components coupled together in a variety of manners that either facilitate or discourage subsequent separation. One or more components or portions of the device can be formed from a radiopaque material to facilitate visualization under fluoroscopy and other imaging techniques, or from a radiolucent material so as not to interfere with visualization of other structures. Example radiolucent materials include carbon fiber and high-strength polymers. Further, various methods of manufacturing can be utilized, including 3D printing or other additive manufacturing techniques, as well as more conventional manufacturing techniques, including molding, stamping, casting, machining, etc.

Various devices or components disclosed herein can be designed to be disposed of after a single use, or they can be designed to be used multiple times. In either case, however, various devices or components can be reconditioned for reuse after at least one use. Reconditioning can include any combination of the steps of disassembly, followed by cleaning or replacement of particular pieces, and subsequent reassembly. In particular, a device or component can be disassembled, and any number of the particular pieces or parts thereof can be selectively replaced or removed in any combination. Upon cleaning and/or replacement of particular parts, the device or component can be reassembled for subsequent use either at a reconditioning facility, or by a surgical team immediately prior to a surgical procedure. Reconditioning of a device or component can utilize a variety of techniques for disassembly, cleaning/replacement, and reassembly. Use of such techniques, and the resulting reconditioned device or component, are within the scope of the present disclosure.

Various devices or components described herein can be processed before use in a surgical procedure. For example, a new or used device or component can be obtained and, if necessary, cleaned. The device or component can be sterilized. In one sterilization technique, the device or component can be placed in a closed and sealed container, such as a plastic or TYVEK bag. The container and its contents can be placed in a field of radiation that can penetrate the container, such as gamma radiation, x-rays, or high-energy electrons. The radiation can kill bacteria on the device or component and in the container. The sterilized device or component can be stored in the sterile container. The sealed container can keep the device or component sterile until it is opened in the medical facility. Other forms of sterilization are also possible, including beta or other forms of radiation, ethylene oxide, steam, or a liquid bath (e.g., cold soak). Certain forms of sterilization may be better suited to use with different devices or components, or portions thereof, due to the materials utilized, the presence of electrical components, etc.

In this disclosure, articles "a" and "an" are used herein to refer to one or to more than one (i.e., at least one) of the grammatical object of the article. By way of example, "an element" means at least one element and can include more than one element. The term "about" is used to provide flexibility to a numerical range endpoint by providing that a given value may be "slightly above" or "slightly below" the endpoint without affecting the desired result. The use herein of the terms "including," "comprising," or "having," and variations thereof, is meant to encompass the elements listed thereafter and equivalents thereof, as well as additional elements. As used herein, "and/or" refers to and encompasses any and all possible combinations of one or more of the associated listed items, as well as the lack of combinations where interpreted in the alternative ("or"). Further, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B," "one or more of A and B," and "A and/or B" are each intended to mean "A alone, B alone, or A and B together." A similar interpretation is also intended for lists including three or more items. For example, the phrases "at least one of A, B, and C," "one or more of A, B, and C," and "A, B, and/or C" are each intended to mean "A alone, B alone, C alone, A and B together, A and C together, B and C together, or A and B and C together." In addition, use of the term "based on," is intended to mean, "based at least in part on," such that an un-recited feature or element is also permissible.

To the extent that linear, circular, or other dimensions are used in the description of the disclosed devices and methods, such dimensions are not intended to limit the types of shapes that can be used in conjunction with such devices and methods. Equivalents to such dimensions can be determined for different geometric shapes, etc. Further, like-numbered components of the embodiments can generally have similar features. Still further, sizes and shapes of the devices, and the components thereof, can depend at least on the anatomy of the subject in which the devices will be used, the size and shape of objects with which the devices will be used, and the methods and procedures in which the devices will be used.

The figures provided herein are not necessarily to scale. Still further, to the extent arrows are used to describe a direction of movement, these arrows are illustrative and in no way limit the direction that the respective component can or should be moved. Other movements and directions may be possible to create the desired result in view of the present disclosure.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

Further features and advantages based on the above-described embodiments are possible and within the scope of the present disclosure. Accordingly, the disclosure is not to be limited by what has been particularly shown and described. All publications and references cited herein are expressly incorporated herein by reference in their entirety, except for any definitions, subject matter disclaimers, or disavowals, and except to the extent that the incorporated material is inconsistent with the express disclosure herein, in which case the language in this disclosure controls.

Examples of the above-described embodiments can include the following:

1. A surgical instrument, comprising:

an inner sleeve having a proximal threaded portion, a distal portion configured to rotate relative to the proximal threaded portion, an inner channel, and a modular drive interface disposed at a proximal end of the threaded portion;

an intermediate sleeve having an inner channel with a threaded proximal portion configured to receive the inner sleeve, the intermediate sleeve terminating in a pair of extensions at a distal end thereof; and an outer sleeve having an inner channel configured to receive the intermediate sleeve, the outer sleeve terminating in a pair of extensions at a distal end thereof;

wherein the pair of extensions of the intermediate sleeve each include a movable arm configured to extend into the inner channel of the intermediate sleeve and facilitate coupling to an implant disposed between the pair of extensions of the intermediate sleeve;

wherein the pair of extensions of the outer sleeve are configured such that, when the outer sleeve is advanced distally relative to the intermediate sleeve, the pair of extensions of the outer sleeve cover the pair of extensions of the intermediate sleeve and prevent the movable arms of the intermediate sleeve from moving radially outward and, when the outer sleeve is retracted proximally relative to the intermediate sleeve, the pair of extensions of the outer sleeve expose the pair of extensions of the intermediate sleeve and allow the movable arms of the intermediate sleeve to move radially outward.

2. The instrument of example 1, wherein the intermediate sleeve includes a longitudinally extending channel formed in an outer surface thereof and the outer sleeve includes a movable arm configured to extend into the channel of the intermediate sleeve to guide movement of the outer sleeve relative to the intermediate sleeve.

3. The instrument of example 2, wherein the channel of the intermediate sleeve includes detents formed at proximal and distal ends thereof configured to preferentially seat the movable arm of the outer sleeve at the proximal and distal ends of the channel.

4. The instrument of example 3, wherein the channel includes a central portion with ramped sidewalls to facilitate ejection of the movable arm of the outer sleeve from the channel of the intermediate sleeve when the portion of the movable arm of the outer sleeve is disposed within the central portion of the channel and the outer sleeve is rotated relative to the intermediate sleeve.

5. The instrument of example 4, further comprising an indicator formed on a surface of the intermediate sleeve that demarcates a position of the outer sleeve relative to the intermediate sleeve wherein the movable arm of the outer sleeve is disposed within the central portion of the channel of the intermediate sleeve.

6. The instrument of any of examples 2 to 5, wherein the intermediate sleeve includes two opposed channels formed in the outer surface thereof and the outer sleeve includes two opposed movable arms configured to extend into the two opposed channels of the intermediate sleeve.

7. The instrument of any of examples 1 to 6, further comprising one or more indicators formed on a surface of the intermediate sleeve that demarcate one or more of a distally advanced position of the outer sleeve relative to the intermediate sleeve and a proximally retracted position of the outer sleeve relative to the intermediate sleeve.

8. The instrument of any of examples 1 to 7, wherein the movable arms of the intermediate sleeve are biased radially inward to facilitate engagement with an implant disposed between the pair of extensions of the intermediate sleeve.

9. The instrument of any of examples 1 to 8, wherein the distal portion of the inner sleeve further comprises a longitudinal groove formed in an outer surface thereof that is configured to receive a feature protruding from an inner surface of the intermediate sleeve to prevent rotation of the distal portion of the inner sleeve relative to the intermediate sleeve.

10. The instrument of any of examples 1 to 9, wherein the inner channel of the inner sleeve is sized to receive a setscrew through a proximal end thereof and allow passage of the setscrew distally through the channel and out a distal end of the inner sleeve.

11. The instrument of any of examples 1 to 10, further comprising a counter-torque device having a mating feature that corresponds to one or more flats formed on the intermediate sleeve.

12. The instrument of any of examples 1 to 11, further comprising an extension sleeve that defines a lumen therethrough, the extension sleeve being configured to couple to the intermediate sleeve, the extension sleeve having one or more engagement surfaces that overlap with one or more flats formed on the intermediate sleeve to facilitate coupling.

13. The instrument of example 12, wherein the extension sleeve further comprises a pair of movable arms that are configured to extend into the lumen to further couple the extension sleeve to the intermediate sleeve.

14. The instrument of example 13, wherein the extension sleeve further comprises a locking ring configured to selectively constrain movement of the movable arms.

15. The instrument of example 13, wherein the movable arms are received in a circumferential groove along the intermediate sleeve.

16 The instrument of any of examples 1 to 15, wherein the threaded portion of the inner sleeve includes a first threaded portion and a second threaded portion separated by a non-threaded portion.

17. The instrument of any of examples 1 to 16, wherein the threaded portion of the inner sleeve is configured to be pulled and rotated to be removed from the intermediate sleeve.

18. The instrument of any of examples 1 to 17, wherein the proximal end portion of the intermediate sleeve includes a circumferential groove.

19. The instrument of any of examples 1 to 18, further comprising a modular handle configured to couple with the modular drive interface at the proximal end of the inner sleeve.

20. The instrument of example 19, wherein the modular handle includes a channel formed therein sized to receive a setscrew through a proximal end thereof and allow passage of the setscrew distally through the channel of the modular handle into the inner channel of the inner sleeve.

21. The instrument of any of examples 1 to 20, wherein the outer sleeve includes at least one flat formed at a proximal end thereof.

22. The instrument of any of examples 1 to 21, wherein each of the pair of extensions of the intermediate sleeve includes sidewalls extending outward from inner surfaces of the pair of extensions at lateral ends thereof.

23. The instrument of example 22, wherein the sidewalls include medially extending protrusions that form a notch between each protrusion and the inner surface.

24. The instrument of example 23, wherein the notch is configured to receive a portion of an implant.

25. A surgical method, comprising:

coupling a surgical instrument to a bone anchor implanted in a vertebra by distally advancing a pair of extensions formed at a distal end of an intermediate sleeve of the surgical instrument over the bone anchor such that movable arms formed in the pair of extensions extend into an inner channel of the intermediate sleeve and interface with a corresponding feature of the bone anchor to retain the implant relative to the intermediate sleeve;

locking the surgical instrument to the implant by distally translating an outer sleeve disposed over the intermediate sleeve to a position where a pair of extensions of the outer sleeve cover the pair of extensions of the intermediate sleeve and prevent the movable arms of the intermediate sleeve from moving radially outward;

reducing a spinal fixation rod disposed between the pair of extensions of the intermediate sleeve toward the bone anchor by rotating a proximal threaded portion of an inner sleeve disposed within the intermediate sleeve such that a distal portion of the inner sleeve contacts the spinal fixation rod and translates distally relative to the intermediate sleeve; and passing a setscrew through an opening in a modular drive interface disposed at the proximal end of the inner sleeve, into an inner channel of the inner sleeve, and coupling the setscrew to the bone anchor after reducing the spinal fixation rod toward the bone anchor.

26 The method of example 25, further comprising performing a derotation maneuver on the vertebra utilizing the surgical instrument coupled to the bone anchor.

27. The method of any of examples 25 to 26, further comprising repeating the steps of the method to couple a plurality of surgical instruments to a plurality of bone anchors disposed in a plurality of vertebrae.

28. The method of any of examples 25 to 27, further comprising unlocking the surgical instrument by proximally translating the outer sleeve relative to the intermediate sleeve to a position where the pair of extensions of the intermediate sleeve are exposed and the movable arms of the intermediate sleeve can move radially outward.

29 The method of example 28, further comprising separating the surgical instrument from the bone anchor by applying a proximal force to the surgical instrument and causing the movable arms of the intermediate sleeve to move radially outward and disengage from the corresponding feature of the bone anchor.

30. The method of example 29, further comprising separating the outer sleeve of the surgical instrument from the intermediate sleeve by positioning the outer sleeve at a midpoint between the distal position where the instrument was locked to the bone anchor and the proximal position where the instrument was unlocked and rotating the outer sleeve relative to the intermediate sleeve.

31. The method of example 30, further comprising applying torque to the outer sleeve utilizing a tool that interfaces with at least one flat formed at a proximal end of the outer sleeve.

32. The method of any of examples 25 to 31, further comprising coupling a counter-torque device to a proximal end of the intermediate sleeve.

33. The method of any of examples 25 to 32, further comprising coupling a derotation sleeve to a proximal end of the intermediate sleeve.

34 The method of any of examples 25 to 33, further comprising pulling and rotating the inner sleeve to remove it from the intermediate sleeve.

35. The method of any of examples 25 to 34, further comprising coupling a modular handle to a proximal end of the intermediate sleeve.

What is claimed is:

1. A surgical instrument, comprising:

an inner sleeve having a proximal threaded portion, a distal portion configured to rotate relative to the proximal threaded portion, an inner channel, and a modular drive interface disposed at a proximal end of the threaded portion;

an intermediate sleeve having an inner channel with a threaded proximal portion configured to receive the inner sleeve, the intermediate sleeve terminating in a pair of extensions at a distal end thereof; and an outer sleeve having an inner channel configured to receive the intermediate sleeve, the outer sleeve terminating in a pair of extensions at a distal end thereof;

wherein the pair of extensions of the intermediate sleeve each include a movable arm configured to extend into the inner channel of the intermediate sleeve and facilitate coupling to an implant disposed between the pair of extensions of the intermediate sleeve;

wherein the pair of extensions of the outer sleeve are configured such that, when the outer sleeve is advanced distally relative to the intermediate sleeve, the pair of extensions of the outer sleeve cover the pair of extensions of the intermediate sleeve and prevent the movable arms of the intermediate sleeve from moving radially outward and, when the outer sleeve is retracted proximally relative to the intermediate sleeve, the pair of extensions of the outer sleeve expose the pair of extensions of the intermediate sleeve and allow the movable arms of the intermediate sleeve to move radially outward, wherein the intermediate sleeve includes a groove formed in an outer surface thereof and the outer sleeve includes a movable arm configured to extend into the groove of the intermediate sleeve to guide movement of the outer sleeve relative to the intermediate sleeve, and wherein the groove of the intermediate sleeve includes detents formed at proximal and distal ends thereof configured to preferentially seat the movable arm of the outer sleeve at the proximal and distal ends of the groove.

2. The instrument of claim 1, wherein the groove includes a central portion with ramped sidewalls to facilitate ejection of the movable arm of the outer sleeve from the groove of the intermediate sleeve when the portion of the movable arm of the outer sleeve is disposed within the central portion of the groove and the outer sleeve is rotated relative to the intermediate sleeve.

3. The instrument of claim 2, further comprising an indicator formed on a surface of the intermediate sleeve that demarcates a position of the outer sleeve relative to the intermediate sleeve wherein the movable arm of the outer sleeve is disposed within the central portion of the groove of the intermediate sleeve.

4. The instrument of claim 1, wherein the movable arm comprises two opposed movable arms, and the groove of the intermediate sleeve comprises two opposed grooves formed in the outer surface thereof through which the two opposed movable arms are configured to extend into the two opposed grooves of the intermediate sleeve.

5. The instrument of claim 1, further comprising one or more indicators formed on a surface of the intermediate sleeve that demarcate one or more of a distally advanced position of the outer sleeve relative to the intermediate sleeve and a proximally retracted position of the outer sleeve relative to the intermediate sleeve.

6. The instrument of claim 1, wherein the movable arms of the intermediate sleeve are biased radially inward to facilitate engagement with an implant disposed between the pair of extensions of the intermediate sleeve.

7. The instrument of claim 1, wherein the distal portion of the inner sleeve further comprises a longitudinal groove formed in an outer surface thereof that is configured to receive a feature protruding from an inner surface of the intermediate sleeve to prevent rotation of the distal portion of the inner sleeve relative to the intermediate sleeve.

8. The instrument of claim 1, wherein the inner channel of the inner sleeve is sized to receive a setscrew through a proximal end thereof and allow passage of the setscrew distally through the inner channel and out a distal end of the inner sleeve.

9. The instrument of claim 1, further comprising a counter-torque device having a mating feature that corresponds to one or more flats formed on the intermediate sleeve.

10. The instrument of claim 1, further comprising an extension sleeve that defines a lumen therethrough, the extension sleeve being configured to couple to the intermediate sleeve, the extension sleeve having one or more engagement surfaces that overlap with one or more flats formed on the intermediate sleeve to facilitate coupling.

11. The instrument of claim 10, wherein the extension sleeve further comprises a pair of movable extension arms that are configured to extend into the lumen to further couple the extension sleeve to the intermediate sleeve.

12. The instrument of claim 11, wherein the extension sleeve further comprises a locking ring configured to selectively constrain movement of the movable extension arms.

13. The instrument of claim 11, wherein the movable extension arms are received in a circumferential groove along the intermediate sleeve.

14. The instrument of claim 1, wherein the threaded portion of the inner sleeve includes a first threaded portion and a second threaded portion separated by a non-threaded portion.

15. The instrument of claim 1, wherein the threaded portion of the inner sleeve is configured to be pulled and rotated to be removed from the intermediate sleeve.

16. The instrument of claim 1, wherein the proximal portion of the intermediate sleeve includes a circumferential groove.

17. The instrument of claim 1, further comprising a modular handle configured to couple with the modular drive interface at the proximal end of the inner sleeve, the modular handle including a channel formed therein sized to receive a setscrew through a proximal end thereof and allow passage of the setscrew distally through the channel of the modular handle into the inner channel of the inner sleeve.

18. The instrument of claim 1, wherein the outer sleeve includes at least one flat formed at a proximal end thereof.

19. The instrument of claim 1, wherein each of the pair of extensions of the intermediate sleeve includes sidewalls extending outward from inner surfaces of the pair of extensions at lateral ends thereof.

20. The instrument of claim 19, wherein the sidewalls include medially extending protrusions that form a notch between each protrusion and the inner surface, the notch being configured to receive a portion of an implant.

\* \* \* \* \*